(12) United States Patent
Ohmiya et al.

(10) Patent No.: US 7,544,484 B2
(45) Date of Patent: Jun. 9, 2009

(54) NUCLEIC ACIDS ENCODING MEMBRANE-BINDING PROTEINS AND METHODS OF USING SAME

(75) Inventors: Yoshihiro Ohmiya, Ikeda (JP); Emiko Ashitaka, Moriguchi (JP); Seiji Ito, Moriguchi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 308 days.

(21) Appl. No.: 10/526,569

(22) PCT Filed: Sep. 4, 2003

(86) PCT No.: PCT/JP03/11285

§ 371 (c)(1),
(2), (4) Date: Mar. 4, 2005

(87) PCT Pub. No.: WO2004/022600

PCT Pub. Date: Mar. 18, 2004

(65) Prior Publication Data

US 2007/0015229 A1    Jan. 18, 2007

(30) Foreign Application Priority Data

Sep. 6, 2002  (JP) ............................. 2002-261229
Dec. 10, 2002 (JP) ............................. 2002-357407

(51) Int. Cl.
*C12P 21/06* (2006.01)

(52) U.S. Cl. ......................... 435/69.1; 435/6; 435/7.1; 435/320; 435/325; 435/252

(58) Field of Classification Search ....................... None
See application file for complete search history.

(56) References Cited

U.S. PATENT DOCUMENTS 5,976,796 A    11/1999   Szalay et al.

FOREIGN PATENT DOCUMENTS

WO    WO 98/14605         4/1998
WO    WO 01/46694 A2      6/2001

OTHER PUBLICATIONS

Richard N. Day, et al., "Dual-Function Reporter Protein for Analysis of Gene Expression in Living Cells," BioTechniques, vol. 25, No. 5, pp. 848-856 1998.
Yoshio Ohmiya, et al., "Shining the light: the mechanism of the bioluminescence reaction of calcium-binding photoproteins," Chemistry & Biology, vol. 3, No. 5, pp. 337-347 1996.
Eric M. Thompson, "Cloning and expression of cDNA for the luciferase from the marine ostracod *Vargula hilgendorfii*," Proc. Natl. Acad. Sci. USA, vol. 86, No. 17, pp. 6567-6571 1989.
Y. A. Yu, et al., "A *Renilla* luciferase-*Aequorea* GFP [*ruc-gfp*] fusion gene construct permits real-time detection of promoter activation by exogenously administered mifepristone in vivo," Mol. Genet. Genomics, 268 (2) pp. 169-178 2002.
Adam Baker, et al., "Delivery of bacterial artificial chromosomes into mammalian cells with psoralen-inactivated adenovirus carrier," Nucleic Acid Research, vol. 25, No. 10, pp. 1950-1956 1997.

*Primary Examiner*—Hope A Robinson
(74) *Attorney, Agent, or Firm*—Wenderoth, Lind & Ponack, L.L.P.

(57) ABSTRACT

A secretory or membrane-binding chimeric protein composed of an energy-generating protein and an energy-receiving protein linked one another wherein energy transfer can arise between the energy-generating protein and the energy-receiving protein.

5 Claims, 11 Drawing Sheets

Plasmid name: pEF-BOS Vluc-EYFP
Plasmid size: 7695 bp

Rluc-EYFP

Vluc-EYFP

1) VL-(Inserted Peptide 1)-YFP
GSTEPGLEEVGEIEQKQLQKRFGGFTGARKSARKLANQGS

2) VL-(Inserted Peptide 2)-YFP
GSLVGQLPGRLPGPGEAPEPLLQLFLLNLPHLLQAGLCGS

VL-Inserted Peptide 1-YFP

GSTEPGLEEVGEIEQKQLQKRFGGFTGARKSARKLANQGS

VL-Inserted Peptide 2-YFP

GSLVGQLPGRLPGPGEAPEPLLQLFLLNLPHLLQAGLCGS

US 7,544,484 B2

NUCLEIC ACIDS ENCODING MEMBRANE-BINDING PROTEINS AND METHODS OF USING SAME

This application is the U.S. National Phase under 35 U.S.C. §371 of International Application PCT/JP2003/011285, filed Sep. 4, 2003, which claims priority to Japanese Patent Application No. 2002-261229, filed Sep. 6, 2002, and No. 2002-357407, filed Dec. 10, 2002. The International Application was not published under PCT Article 21(2) in English.

TECHNICAL FIELD

The present invention relates to a secretory or membrane-binding chimeric protein, a gene encoding the protein, a method for measuring or evaluating a gene transcription activity in a cell and a method for screening a drug which regulates gene expression. The invention also includes a method for screening a drug which regulates gene transcription expression and an enzyme activity of an enzyme which regulates protein modification.

The chimeric protein of the invention can take advantage of an energy transfer property between an energy-generating protein and an energy-receiving protein.

BACKGROUND ART

A phenomenon of energy transfer which occurs between a light-emitting enzyme and a fluorescent protein is a natural phenomenon which occurs in luminescent jellyfishes and luminescent mushrooms, and a mechanism thereof has been elucidated at a molecular level (Ohmiya, Y. and Hirano, T: Shining the light: the mechanism of the bioluminescence reaction of calcium-binding photoproteins. Chemistry & Biology 3:337-347, 1996). Furthermore, a *Renilla* luciferase and green fluorescent protein fusion gene which simulates this natural phenomenon has been constructed, and a method for quantitatively and qualitatively monitoring the gene expression using a luciferase activity and a fluorescent activity has been known (U.S. Pat. No. 5,976,796 and WO98/14605).

The *Renilla* luciferase is an enzyme purified from *Renilla reniformis*. This enzyme catalyzes oxidative decarboxylation of a luminescent substrate, coelenterazine in the presence of the enzyme to produce blue light with a maximum wavelength of 478 nm. However, in the natural world, the light shifts to green light having the maximum wavelength of 510 nm attributed to the energy transfer to a green fluorescent protein present in *Renilla reniformis*. A *Renilla* luciferase gene has been already cloned, and a cDNA thereof has been shown to be useful as a reporter gene for measuring a transcription activity of a gene.

The fluorescent protein sometimes coexists with the light-emitting enzyme as those in the luminescent jellyfish and luminescent *Renilla* whereas it sometimes singly exists as that in cactuses. A green fluorescent protein purified from the luminescent jellyfish, *Aequorea victoria* receives blue light from a photoprotein, and converts this to green light. This gene has been cloned, and is a strong reporter gene in various biological systems (bacterial, fungal and mammalian tissues) because green fluorescence is emitted by blue excitation light without need of a cofactor when a cDNA thereof is expressed in a cell. In modified types of a wild-type green fluorescent protein, there are a modified one having a shift toward a red with blight luminescence and a modified one whose stability is improved in mammalian cells. A cDNA of a red fluorescent protein has been also cloned from a naturally occurring coral, and is also useful as the reporter gene.

A construct of the *Renilla* luciferase and green fluorescent protein fusion gene previously invented is distributed in an entire cytoplasm depending on a character of *Renilla* luciferase, and is not localized. A luminescent substrate of the *Renilla* luciferase has no cell permeability, and the gene expression can not be detected unless the cells are once lysed.

A luminescent crustacean, marine ostracod, *Vargula hilgendorfii* and its related species *Cypridina noctiluca* have a secretory light-emitting enzyme, and a cDNA of the *Vargula* luciferase has been already cloned. It reacts with a marine ostracod luminescent substrate, *Cypridina* luciferin to emit blue light with a maximum luminescent wavelength of 460 nm. A gene transcription activity can be measured without lysing the cells because the cloned cDNA works as the reporter gene and the light-emitting enzyme is secreted out of the cells. The secretion of a protein from the cells can be visualized by image-analyzing of this secretory light-emitting enzyme. Meanwhile, it emits the blue light, but it has been never practically applied as a donor protein of energy transfer.

It is an object of the present invention to construct a secretory or membrane-binding protein fusion having an energy transfer property, make and use a construct having two functions of an energy-generating protein and an energy-receiving protein measurable out of a cell or on a cell surface. A gene transcription activity can be measured out of the cell as the energy transfer property, and together, a secretory pathway from an inside to an outside of the cell can be evaluated by the energy transfer property. A peptide three dimensional structure information can be obtained by inserting a monitor peptide between the energy-generating protein and the energy-receiving protein or inside the energy-generating protein or the energy-receiving protein of the secretory or membrane-binding chimeric protein, and using a change of the energy transfer by cutting the monitor peptide as an indicator. In particular, when a light-emitting enzyme and a fluorescent protein are used as the energy-generating protein and the energy-receiving protein, a fusion construct capable of measuring fluorescence without using excitation light can be made because the fluorescent protein is excited with the light emitted from the light-emitting enzyme and a color of the emitted light is changed by the energy transfer.

BRIEF DESCRIPTION OF THE DRAWINGS

In FIG. 9, the secretory protein is an energy-generating protein.

In FIG. 10, a membrane-binding region is present inside an energy-generating protein. The membrane-binding region may be in a monitor peptide or an energy-receiving protein.

DISCLOSURE OF THE INVENTION

Figure 1A:
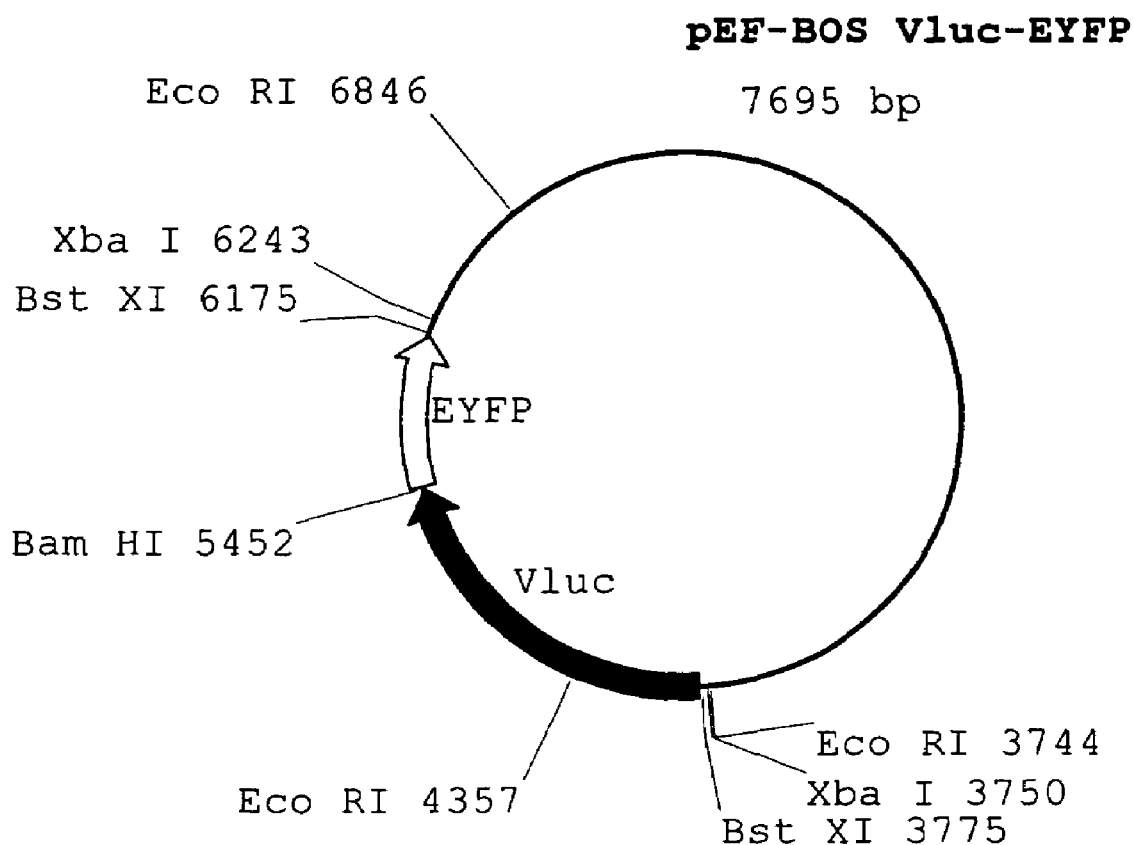
FIG. 1a shows a construction of a luminescent fluorescent fusion protein vector in which a *Vargula* luciferase gene (Vluc) and a mutant yellow fluorescent protein gene (EYFP) amplified by PCR were inserted into an expression vector for mammalian cells, PEF-BOS.

As a result of an intensive study for solving the above problems, the present inventor has constructed a gene where an energy-generating protein and an energy-receiving protein are fused, and thereby completed the present invention.

The present gene was obtained by fusing the proteins already described in a gene database, but this combination is unknown. As described later, the present inventor has first expressed/analyzed a fusion construct and demonstrated that it comprises three properties, i.e., a secretory or membrane-binding property, an energy-generating (e.g., luminescence) property and an energy-receiving (e.g., fluorescence) property. The present inventor has also first demonstrated that energy transfer arises even in a combination of a secretory light-emitting enzyme (*Vargula* luciferase) which is not originally present in the biological world with a fluorescent protein (YFP).

(1) A secretory or membrane-binding chimeric protein composed of an energy-generating protein and an energy-receiving protein linked one another wherein energy transfer can arise between the energy-generating protein and the energy-receiving protein.

(2) The secretory or membrane-binding chimeric protein according to (1) having any structure of the following 1) to 6):
1) [secretory energy-generating protein]-[energy-receiving protein];
2) [secretory energy-receiving protein]-[energy-generating protein];
3) [membrane-binding energy-generating protein]-[energy-receiving protein];
4) [membrane-binding energy-receiving protein]-[energy-generating protein];
5) [signal peptide]-[energy-generating protein]-[energy-receiving protein]; and
6) [signal peptide]-[energy-receiving protein]-[energy-generating protein].

(3) The chimeric protein according to (1) wherein a monitor peptide is introduced between the energy-generating protein and the energy-receiving protein or inside the energy-generating protein or inside energy-receiving protein so as to retain an energy-generating property or an energy-receiving property, and the energy transfer is inhibited by cleaving the monitor peptide.

(4) The chimeric protein according to any of (1) to (3) wherein the energy-generating protein is a photoprotein.

(5) The chimeric protein according to (4) wherein the photoprotein is luciferase.

(6) The chimeric protein according to any of (1) to (3) wherein the energy-receiving protein is a fluorescent protein or a colored protein.

(7) The chimeric protein according to (6) wherein the fluorescent protein is GFP, YFP, BFP, CFP, DsRED or RFP.

(8) The chimeric protein according to (1) having an amino acid sequence represented by SEQ ID NO:1.

(9) A polynucleotide encoding the secretory or membrane-binding chimeric protein according to any of (1) to (8), or a complementary chain thereof.

(10) A vector comprising the polynucleotide according to (9).

(11) A transformant transformed with the vector according to (10).

(12) A method for producing a secretory or membrane-binding chimeric protein including a step of culturing the transformant according to (11) in a medium, and a step of collecting the secretory or membrane-binding chimeric protein from the medium.

(13) A method for measuring (evaluating) a gene transcription activity in a host cell, characterized in that the transformant according to (11) is cultured and energy transfer in a secretory or membrane-binding chimeric protein secreted in a medium or bound to a cell membrane is quantified.

(14) A method for screening a drug which regulates gene expression in a cell, including a step of culturing the transformant according to (11) in the presence of a drug candidate compound in a medium, and a step of quantitatively comparing energy transfer in a secretory or membrane-binding chimeric protein secreted in the medium or bound to a cell membrane in the presence or absence of the candidate compound.

(15) The method according to (14) wherein the drug which regulates the gene expression in the cell is a drug which regulates gene transcription expression or an enzyme activity of an enzyme which regulates protein modification.

(16) The method according to (14) wherein the transformant comprises a polynucleotide sequence represented by SEQ ID NO:1.

The present invention will be illustrated below.

The chimeric protein of the present invention is characterized in that intramolecular energy can be transferred. Intramolecular energy transfer means that the energy transfer arises between energy (e.g., light energy) emitted from an energy-generating protein (e.g., biological photoprotein) and an energy-receiving protein (fluorescent protein, colored protein). As a result of the energy transfer, for example, a fluorescent protein can emit fluorescence without requiring external light, and this enables to quantify a level of the energy transfer.

As the energy-generation protein, preferably a biological photoprotein (light-emitting enzyme such as luciferase) is exemplified.

As the energy-receiving protein, a fluorescent protein and a colored protein are exemplified. The energy-receiving protein is a protein capable of confirming energy reception, and for example in the fluorescent protein, the level of the energy transfer can be quantified by measuring the fluorescence.

The present invention will be more specifically illustrated below with reference to an example using a secretory biological photoprotein as the energy-generating protein and a fluorescent protein as the energy-receiving protein.

The chimeric protein is secretory, and an existence thereof can be easily detected with fluorescence by giving luciferin out of cells. Even if the chimeric protein is a membrane-binding protein, it can be similarly detected by giving the luciferin.

In the fluorescent protein such as GFP alone, a qualitative analysis by the fluorescence is possible, but a quantitative analysis is impossible because the fluorescence is emitted by external excitation light. On the other hand, in the chimeric protein of the present invention, it is possible to quantify each modification (cleavage of monitor peptide, modification by sugar chain, etc.) based on a shift of a fluorescence wavelength thereof because the fluorescent protein emits the fluorescence by an excitation light from the biological photoprotein.

In the present invention, a monitor protein is not particularly limited as long as it does not prevent the energy transfer from the biological photoprotein to the fluorescent protein. A number of amino acid residues of the monitor peptide is usually 5 to 100, preferably 6 to 50, more preferably 6 to 20, and particularly 6 to 15. It is preferable to introduce the monitor peptide at a position at which no energy transfer arises by cleavage thereof. As an introduced position of the monitor peptide, it is exemplified that the monitor peptide is introduced between the energy-generating protein and the energy-receiving protein, or inside the energy-generating protein, or inside the energy-receiving protein. It is preferable to introduce it between the energy-generating protein and the energy-receiving protein. When the monitor peptide is introduced inside the energy-generating protein, an energy-generating property remains after the introduction and a luminescence property thereof is lost by cleaving the monitor peptide. Likewise, when the monitor peptide is introduced inside the energy-receiving protein, an energy-receiving property remains after the introduction and an energy-receiving property (e.g., fluorescence property) thereof is lost by cleaving the monitor peptide.

If a restriction enzyme site is introduced in the monitor peptide, the production of the chimeric protein becomes easier. If a proteolytic site for a certain protease is introduced in the monitor peptide, an action of the protease in a secretory process can be quantified, and it becomes possible to quantitatively screen substances which affect functions of processing enzymes of various secretory proteins. One of the preferable monitor peptide sequences is a sequence (spacer peptide sequence 1) composed of 40 amino acid residues represented by SEQ ID NO:4.

As another monitor peptide, a sequence represented by SEQKQLQKRFGGFTGG (SEQ ID NO:10) which is a partial sequence of a naturally occurring protein where a C terminus side of R can be cleaved by a processing enzyme PC1 is exemplified. The inventor has confirmed that the chimeric protein having this monitor peptide sequence has the energy transfer property and the energy transfer property is lost by cleaving the C terminus side of R of the sequence.

On the other hand, the chimeric protein having a spacer sequence 2 which is a non-naturally occurring polypeptide produces no energy transfer.

This way, in order to enable the energy transfer between the energy-generating protein and the energy-receiving protein, it is preferable that the monitor peptide has a partial amino acid sequence of a naturally occurring polypeptide or an analogous sequence to an amino acid sequence of the naturally occurring polypeptide. By making the naturally occurring polypeptide or a partial sequence thereof the monitor peptide, obviously the property of the naturally occurring sequence (e.g., a cleaving property of various proteases including the processing enzyme [PC1, PC2, furin, proteasomes, cathepsin, thrombin, etc.], a substrate of an enzyme, an agonist/antagonist of receptor, or a binding property of a binding factor such as protein, sugar and low molecular substance) can be measured or evaluated based on the change of the energy transfer.

As used herein, as biological photoproteins, luciferases derived from various luminescent organisms such as *Cypridina hilgendorfii* (marine ostracod), *Acanthephya purpurea*, luminescent insects (firefly, headlight beetle, etc.), luminescent earthworm, *Latia neritoides, Renilla, Aequorea coerulescens* (aequorin) and the like are exemplified. For example, the *Vargula* luciferase is a secretory type, and thus the intact luciferase can be used as the secretory biological photoprotein. In the case of non-secretory luciferase such as luciferase from *Renilla*, it can be also used as the secretory biological photoprotein by introducing a signal peptide into an N terminus side.

As the fluorescent protein, a green fluorescent protein (GFP), a yellow fluorescent protein (YFP), a blue fluorescent protein (BFP), a cyan fluorescent protein (CFP), DsRED, a red fluorescent protein (RFP) and the like are exemplified.

As the colored protein, phycocyanin and phycoerythrin are included.

The fluorescent protein or colored protein of the present invention is selected such that the light emitted from the biological photoprotein has an excitation wavelength of the fluorescent protein or an absorption wavelength of the colored protein. Such combinations include the followings.

TABLE 1

| Biological photoprotein | Fluorescent protein or colored protein |
|---|---|
| *Vargula* luciferase | GFP, YFP, BFP, CFP, DsRED, RFP |
| Firefly luciferase | DsRED, phycocyanin, phycoerythrin |
| Luminescent dinoflagellate luciferase | GFP, YFP, BFP, CFP, DsRED, RFP |
| Headlight beetle luciferase | DsRED |
| *Renilla* luciferase | GFP, YFP, BFP, CFP, DsRED, RFP |
| Aequorin | GFP, YFP, BFP, CFP, DsRED, RFP |

The secretory biological photoprotein and the fluorescent protein may be directly linked, or may be linked through the monitor peptide between the both.

The chimeric protein of the present invention includes the proteins represented by the following 1) to 3).

1) A secretory chimeric protein where a fluorescent protein is attached to the C terminus of a secretory biological photoprotein. One preferable embodiment of the protein is the protein represented by the amino acid sequence in SEQ ID NO:1.
2) A fused construct represented by an amino acid sequence having one or more deletions, substitutions, or additions in the amino acid sequence in SEQ ID NO:1, and having a secretory property, a light-emitting enzyme activity, a photoprotein activity and an energy transfer activity.
3) A protein where a mutation is introduced into the protein of the above 1) at a level at which the secretory property, the light-emitting enzyme activity, the photoprotein activity and the energy transfer activity are not lost. Such a mutation includes an artificial mutation in addition to a naturally occurring mutation (e.g., allele). A procedure for causing the artificial mutation can include a site-directed mutagenesis method (Nucleic Acids Res., 10:6487-6500, 1982), but is not limited thereto. A number of mutated amino acid residues is not limited as long as the secretory, light-emitting, fluorescent activities and the energy transfer property are not lost, but is preferably within 20, more preferably within 15, still more preferably within 10 and most preferably within 5 amino acid residues in the light-emitting enzyme and fluorescent protein portions. In the monitor peptide to which the light-emitting enzyme and the fluorescent protein are attached, the substitution, the deletion, the addition or the insertion can be optionally introduced for 1 to 100 amino acid residues. When the mutation is introduced by such a substitution, deletion, addition or insertion, it can be determined whether the protein in which the mutation has been introduced retains the light-emitting/fluorescent activities, by examining the light-emitting/fluorescent activities of the protein.

The polynucleotide of the present invention includes a polynucleotide encoding the secretory or membrane-binding chimeric protein where the fluorescent protein has been attached to the C terminus or N terminus side of the secretory biological photoprotein. One preferable embodiment of the polynucleotide includes a DNA represented by a nucleotide sequence described in SEQ ID NO:1 or 2, or a DNA which hybridizes with a complementary chain thereof under a stringent condition. A protein encoded by the DNA is a fused molecule having the secretory activity, the light-emitting enzyme activity, the fluorescent protein activity and the energy transfer activity.

The protein encoded by the above DNA is a protein having a secretory light-emitting enzyme activity, the fluorescent protein activity and the energy transfer activity, obtained by taking advantage of hybridization of DNA one another. Herein, the "stringent condition" refers to a condition where a specific hybridization is formed whereas non-specific hybridization is not formed. Such a condition is about "1×SSC, 0.1% SDS and 37° C.", preferably about "0.5×SSC, 0.1% SDS and 42° C." and more preferably about "0.2×SSC, 0.1% SDS and 65° C.". A DNA obtained by hybridization with the polynucleotide described in SEQ ID NO:1 or 2 usually has high homology with a DNA represented by the nucleotide sequence described in SEQ ID NO:1 or 2. The high homology indicates 60% or more, preferably 75% or more, more preferably 90% or more and particularly 95% or more homology.

The protein of the present invention can be obtained by incorporating a gene of the invention described later into an expression vector and expressing in appropriate host cells. As the expression vector, for example, pBT-VL-mp-YFP (VL, mp and YFP represent the *Vargula* luciferase, the monitor peptide and the yellow fluorescent protein, respectively) can be used. The host cells include, eukaryotic cells such as mammalian cells and yeast, and prokaryotic cells such as cells of *Escherichia coli, Bacillus subtilis*, algae and fungi, and any of them may be used. As the preferable host cell, a mammalian cultured cell, COS7 cell line (in this system, it is important to experience a protein synthesis process and a protein modification process of a mammalian system, and these processes are monitored) and the like can be used.

The gene (polynucleotide) encoding the preferable chimeric protein of the present invention is:
1) a gene having a nucleotide sequence described in SEQ ID NO:1; and
2) a gene having a DNA which hybridizes with a DNA represented by the nucleotide sequence described in SEQ ID NO:1 or a DNA complementary thereto under the stringent condition.

Figure 8:
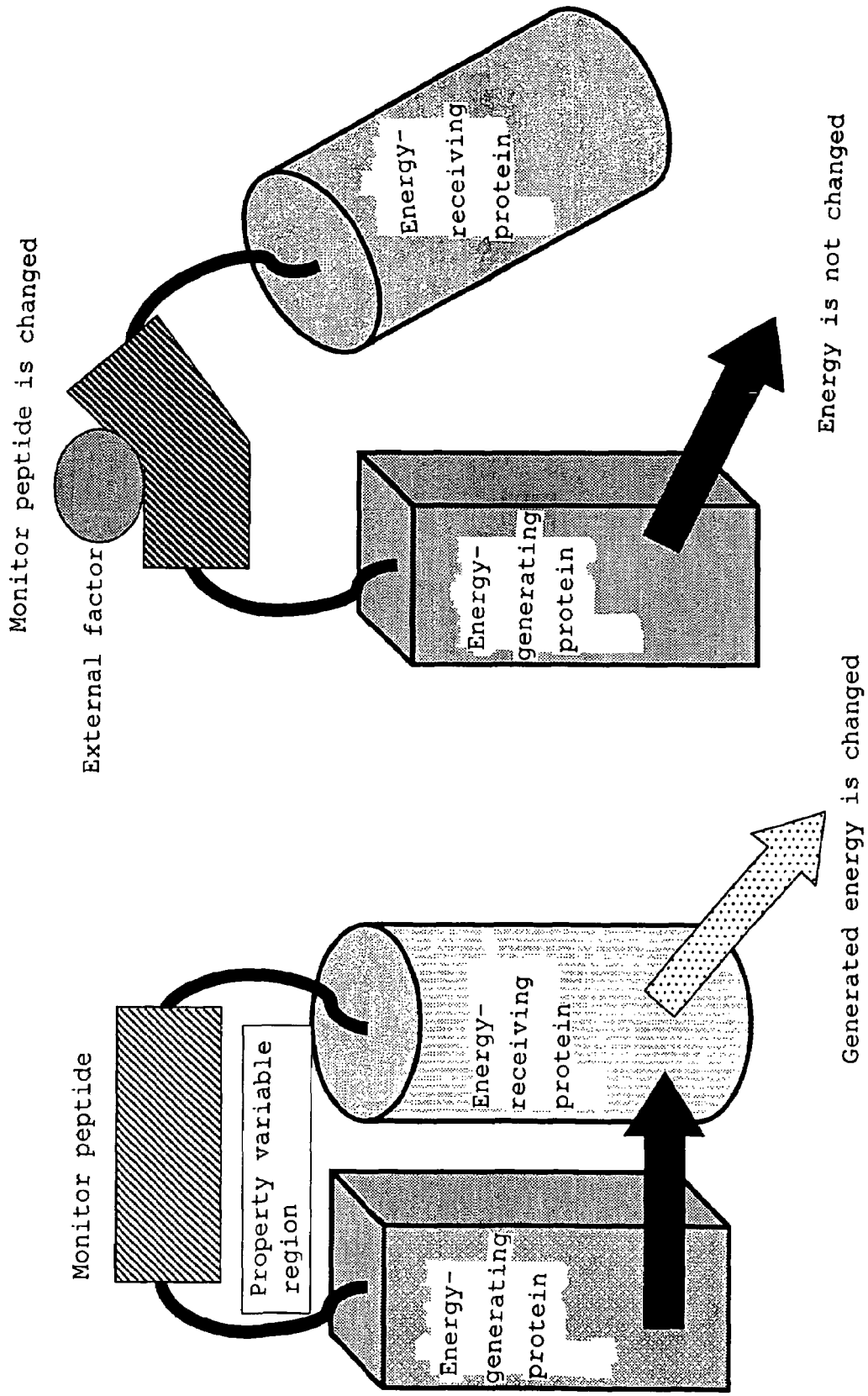
FIG. 8 shows a scheme of the present invention. There exist a secretory type and a membrane-binging type in energy-generating proteins. In the chimeric protein of the invention, energy transfers from the energy-generating protein to an energy-receiving protein (black arrow), and it becomes possible to detect the energy such as light (white arrow) from the energy-receiving protein. Meanwhile, when a three dimensional structure of the chimeric protein is changed by binding an external factor to a monitor peptide or cleaving the monitor peptide, the energy from the energy-generating protein does not reach the energy-receiving protein.
Figure 9:
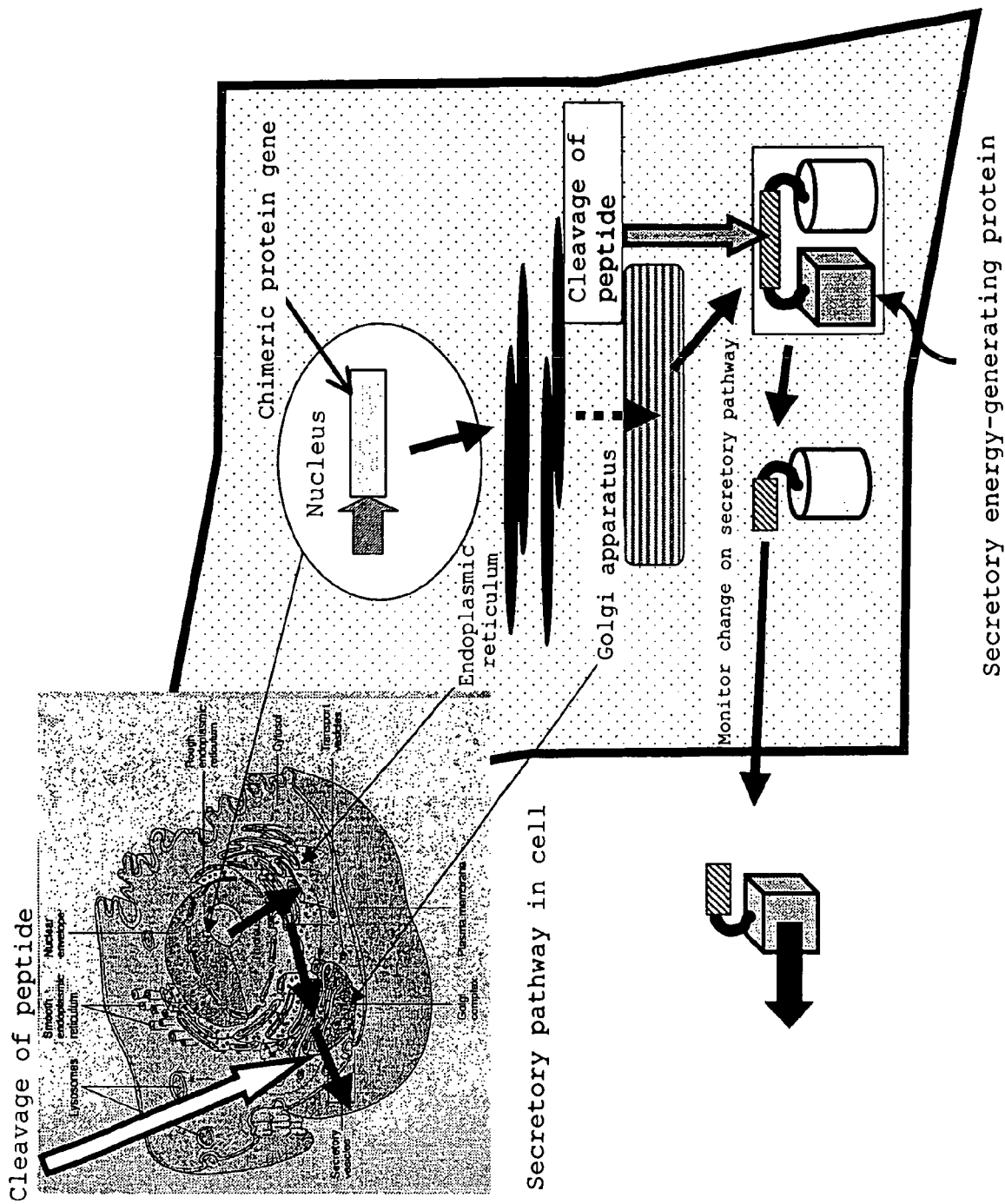
FIG. 9 shows a system example of a secretory chimeric protein.
Figure 10:
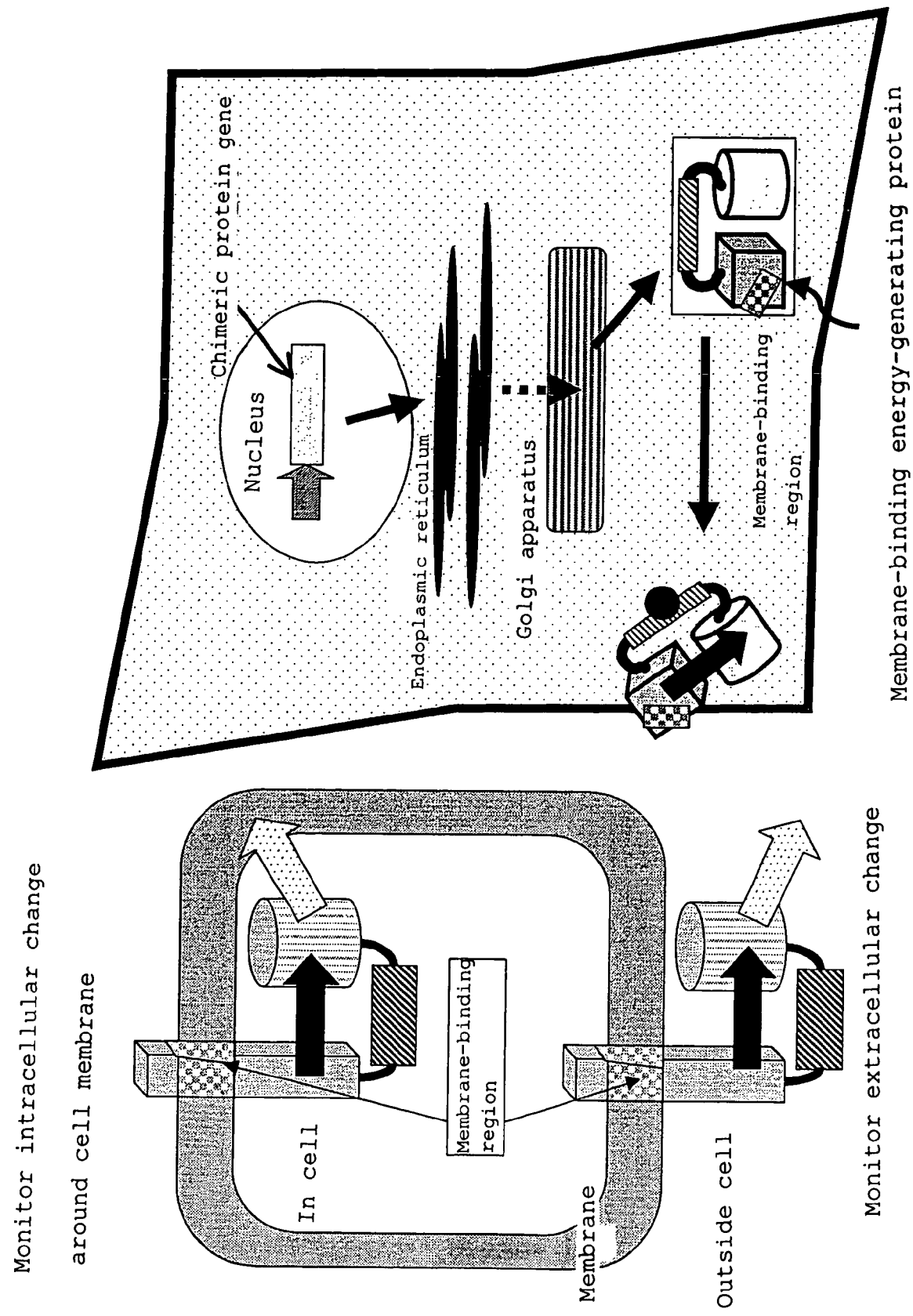
FIG. 10 shows a system example of a membrane-binding chimeric protein.

Schematic views of the system of the present invention are shown in FIGS. 8 to 10. As shown in FIG. 8, in the chimeric protein of the invention, in the case of no structural change of the monitor peptide, the energy transfers from the energy-generating protein to the energy-receiving protein as shown by a black arrow, and it becomes possible to detect the energy (white arrow) such as light from the energy-receiving protein. On the other hand, when the three dimensional structure of the chimeric protein is changed by binding an external factor to the monitor peptide or cleaving the monitor peptide, the energy from the energy-generating protein does not reach the energy-receiving protein. The energy emitted from the chimeric protein is different in energy (white arrow in FIG. 8) through the energy-receiving protein and energy (black arrow in FIG. 8) directly emitted from the energy-generating protein. Therefore, it is possible to quantify a level of an effect of a factor which affects the chimeric protein by measuring the energy from the chimeric protein. For example, when the factor is a candidate compound for a drug, the chimeric protein of the invention is useful for a screening system of the drug as shown below.

As shown in FIG. 9, when the energy-generating protein in the chimeric protein of the present invention is a secretory protein, it is useful for monitoring a change on a secretory pathway of a processing enzyme activity. As is also shown in FIG. 10, when the chimeric protein of the invention is a membrane-binding protein, it is useful for monitoring an intracellular or extracellular change around the membrane.

(Screening Method)

By culturing a transformant in which the gene encoding the chimeric protein of the present invention is incorporated, it is possible to quantitatively measure (evaluate) a gene transcription activity in a host cell, and screen a drug which regulates the gene expression in the cell.

By introducing the chimeric protein of the present invention into the cells and tracking a fluorescence intensity and a shift of a wavelength, it can be examined whether mechanisms of synthetic rate of a protein from mRNA, folding and processing of the synthesized protein, membrane-binding or secretion of the protein in the cells are normally operated.

Therefore, by comparing results obtained by culturing the transformant capable of expressing the chimeric protein of the invention in the presence or absence of a candidate compound for a drug, it can be found what action the candidate compound gives to a protein expression system, and it is possible to select the candidate compound which acts upon the protein expression system (gene expression system).

Compared subjects include a total amount of fusion protein expression, comparison of an intracellular and extracellular expression amounts of the fusion protein, shift levels of the fluorescence wavelength of the fusion protein for the fluorescent protein, levels of a cleavage or a sugar chain bond of the monitor peptide, and the like.

For example, some patients with diabetes have a processing abnormality from proinsulin to insulin, i.e., can not synthesize active insulin due to a mutation of an amino acid residue at a cut site and a low activity of a limited proteolytic enzyme. A drug which normalizes such a processing abnormality is useful as a drug for treating the diabetes.

As peptide hormones whose common precursor is pro-opiomelanocortin (POMC), there are ACTH, β-lipotropin (βLPH), α and β melanocyte stimulating hormones (MSH), enkephalin and endorphin. By affecting a cleaving process from POMC to an active peptide, it is possible to use as a screening system of an anti-inflammatory agent with a cut out of ACTH as an indicator or an analgesic agent with a cut out of endorphin as an indicator.

Since the secretory chimeric protein of the present invention is secreted out of the cells, the biological photoprotein and the fluorescent protein can be each independently quantified by adding a luminescent substrate (luciferin) in the culture medium. Levels of luminescence of the biological photoprotein and the fluorescent protein are remarkably affected by cleavage of the fluorescent protein, cleavage of the monitor protein and sugar chain modification, and thus, it can be quantitatively evaluated how the drug candidate compound affects the gene expression system by the screening system of the present invention.

Since the chimeric protein of the present invention is secreted out of the cells, a luminescence spectrum and a luminescence activity can be measured by adding the luminescent substrate (luciferin) into the culture medium without lysing the cells, and the energy transfer which arises between the biological photoprotein and the fluorescent protein can be quantified. The secreted fusion protein is highly modified through a physiological secretory process in the cells. The energy transfer which arises between the biological photoprotein and the fluorescent protein is remarkably changed and a shape of the luminescence spectrum is changed by cleavage and sugar chain modification of the monitor peptide. For example, the energy transfer disappears along with the cleavage of the monitor peptide, and the energy transfer is increased/decreased by the sugar chain modification. Thus, by the screening system of the present invention, it can be quantitatively evaluated what levels of the effect the drug candidate compound gives to an enzyme activity of a protein modifying enzyme which cleaves or modifies a sugar chain and the gene expression thereof.

BEST MODE FOR CARRYING OUT THE INVENTION

The present invention will be illustrated in more detail with reference to the following Examples, but the invention is not limited thereto.

EXAMPLE 1

Figure 1B:
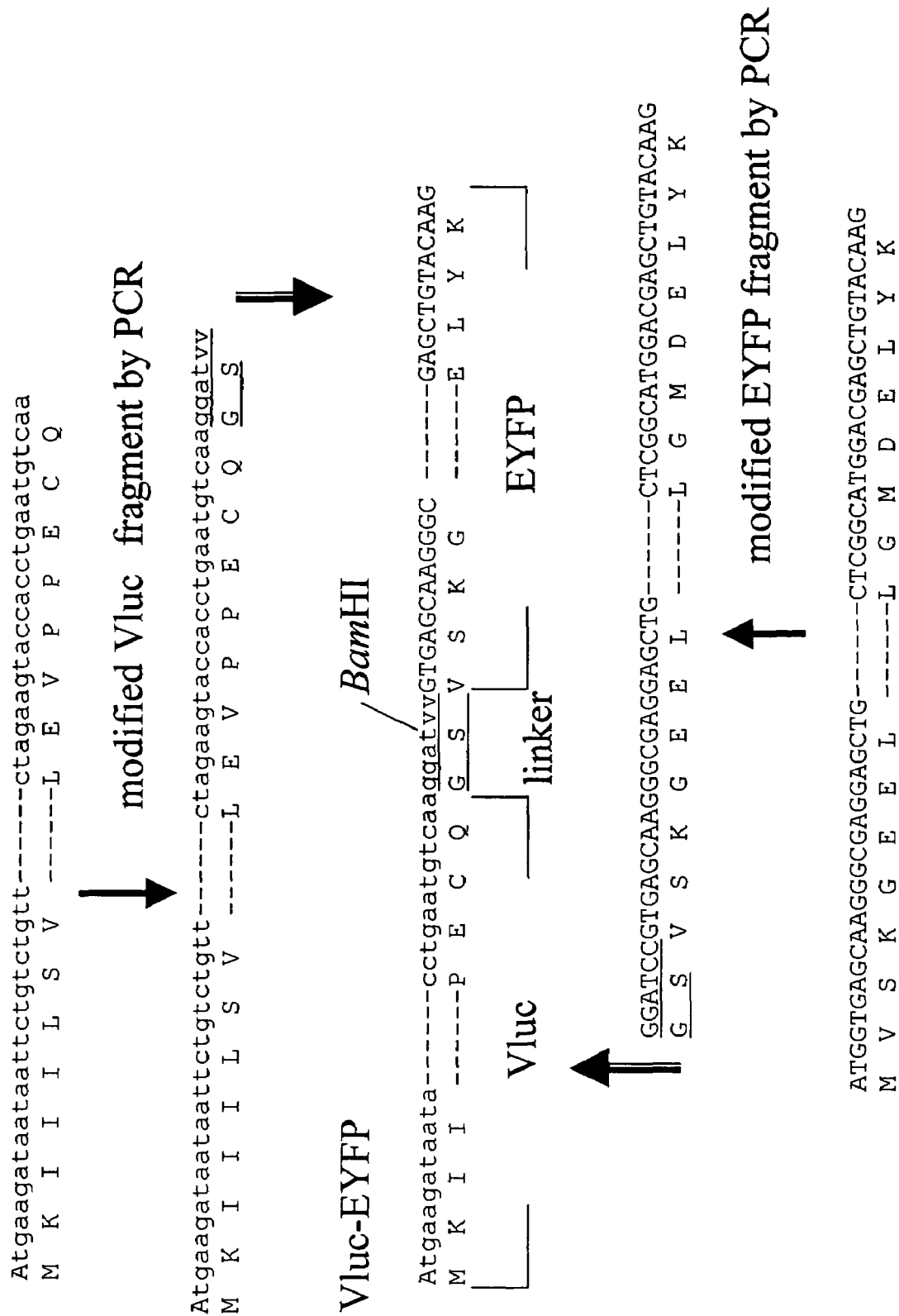
FIG. 1b shows a luminescent fluorescent fusion protein of a *Vargula* luciferase gene (Vluc) and a mutant yellow fluorescent protein gene (EYFP) inserted into an expression vector for mammalian cells, pEF-BOS. The DNA sequence encoding the Vluc fusion protein is shown spanning from the amino terminus (SEQ ID NO: 11) to the carboxy terminus (SEQ ID NO: 12). The corresponding amino acid sequences are shown for the amino terminus (SEQ ID NO: 13) and the carboxy terminus (SEQ ID NO: 14). The DNA sequence encoding the modified Vluc fragment by PCR is shown spanning from the amino terminus (SEQ ID NO: 11) to the carboxy terminus (SEQ ID NO: 15). The corresponding amino acid sequences are shown for the amino terminus (SEQ ID NO: 13) and the carboxy terminus (SEQ ID NO: 16). The DNA sequence encoding Vluc-EYFP is shown spanning from the amino terminus (SEQ ID NO: 17), the linker (SEQ ID NO: 18) and the carboxy terminus (SEQ ID NO: 19). The corresponding amino acid sequences are shown for the amino terminus (SEQ ID NO: 20), the linker (SEQ ID NO: 21) and the carboxy terminus (SEQ ID NO: 22). The DNA sequence encoding the modified EYFP fragment by PCR is shown spanning from the amino terminus (SEQ ID NO: 23) to the carboxy terminus (SEQ ID NO: 24). The corresponding amino acid sequences are shown for the amino terminus (SEQ ID NO: 25) and the carboxy terminus (SEQ ID NO: 26). The DNA sequence encoding the amino terminus of EYFP fragment is shown spanning from the amino terminus (SEQ ID NO: 27) to the carboxy terminus (SEQ ID NO: 28). The corresponding amino acid sequences are shown for the amino terminus (SEQ ID NO: 29) and the carboxy terminus (SEQ ID NO: 30).

Fragments of *Vargula* luciferase (hereinafter, sometimes abbreviated as "VL" or "Vluc") gene (Thompson, E. M., Nagata, S. & Tsuji, F. I. Cloning and expression of cDNA for the luciferase from the marine ostracod *Vargula hilgendorfii*. Proc. Natl. Acad. Sci. USA 86:6567-71, 1989) and a mutant yellow fluorescent protein (EYFP) gene derived from a luminescent jellyfish were amplified by a polymerase chain reaction (PCR method), and inserted into an expression vector for mammals to construct a luminescent/fluorescent fusion protein gene. FIG. 1 shows a map of the vector and an alignment of gene portions. When the Vluc fragment was amplified by PCR, using a primer 1 (5'-(HindIII-BstXI): CAC AAGCTTCCATTGTGCTGGATGAAGATAATAATTCTG-TCTGTTATATTGGC-3'; primer 2 (5'-(BamHI): TGT GGATCCTTGACATTCAGGTGGTACTTCTAG-3', an initiation codon was given to the N-terminus of Vluc, a termination codon was deleted from the C-terminus, and a linker sequence containing a BamHI site was introduced. Meanwhile, for the PCR amplification of the EYFP fragment, a primer 3 (5'-(HindIII-NotI-BamHI): CAAGCTTGCGGCCGCAGGATCCGTGAGCAA GGGC-GAGGAGCTGTTCAC-3'), a primer 4 (5'-(BstXI) TA-CCATTGTGCTGGATGGTGAGCAAGGGCGAGGAGCT-G-3') were used, the initiation codon was deleted from the N-terminus of EYFP, the linker sequence containing a BamHI site was ligated to the N-terminus, and the termination codon was introduced at the C-terminus. The above PCR products were sequentially inserted into a BstXI site of pEF-BOS (S Mizushima & S Nagata pEF-BOS, a powerful mammalian expression vector. Nucleic Acids Research, Vol. 18, No.17 P.5322) already known publicly as the expression vector for the mammals to make an expression vector, and designated as pEF-BOS Vluc-EYFP. In this vector, the *Vargula* luciferase gene was arranged upstream, the mutant yellow fluorescent protein gene from the luminescent jellyfish was arranged downstream, and a peptide sequence can be inserted at a BamHI restriction enzyme site between them.

EXAMPLE 2

Figure 2:
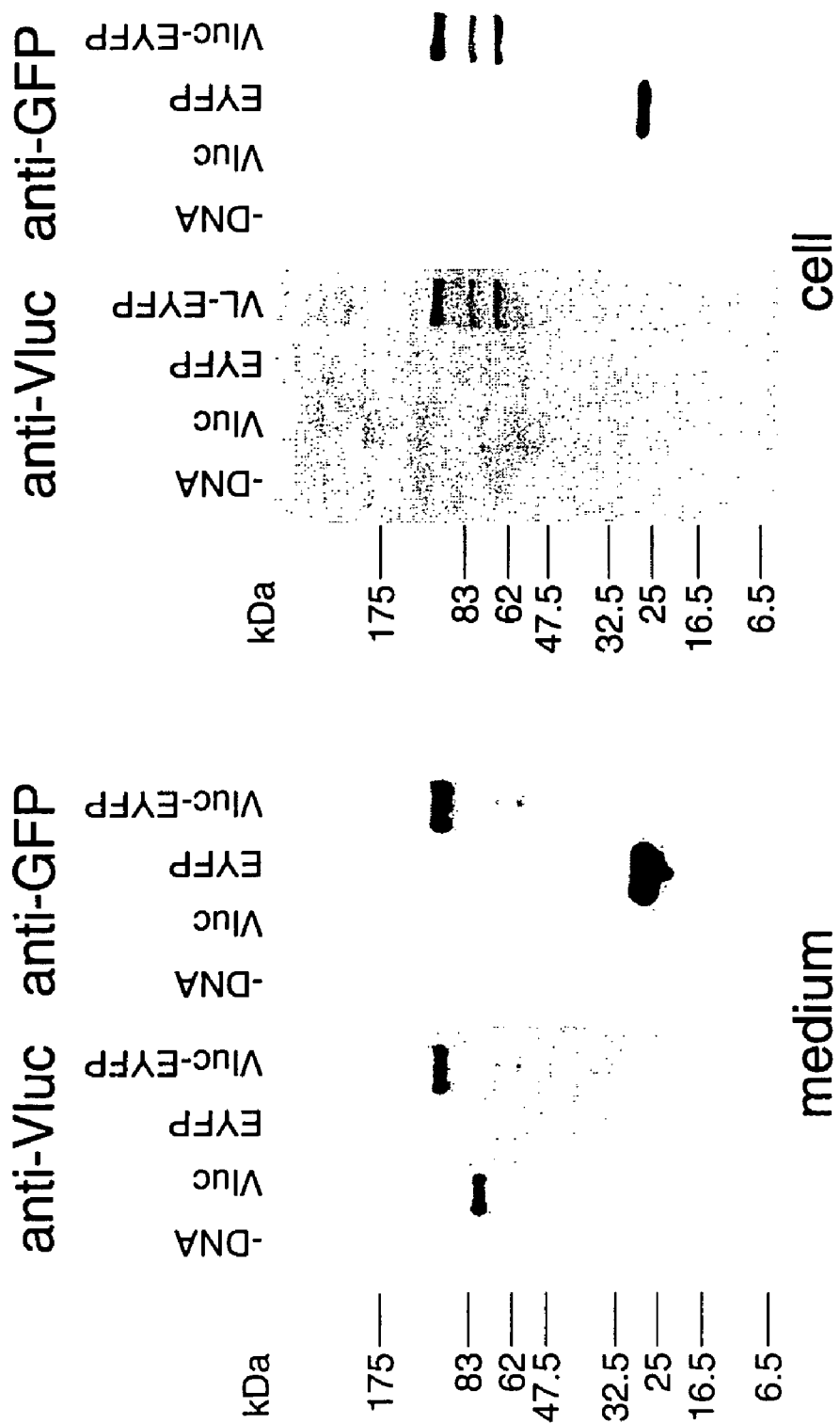
FIG. 2 shows Western blot analyses in and out of cells in which a secretory luminescent fluorescent fusion protein (Vluc-EYFP) is introduced.
Figure 3:
FIG. 3 shows fluorescent images of Cos cells in which a luminescent fluorescent fusion protein molecular probe of a secretory (Vluc-EYFP) type or a non-secretary (Rluc-EYFP) type is introduced.
Figure 3:
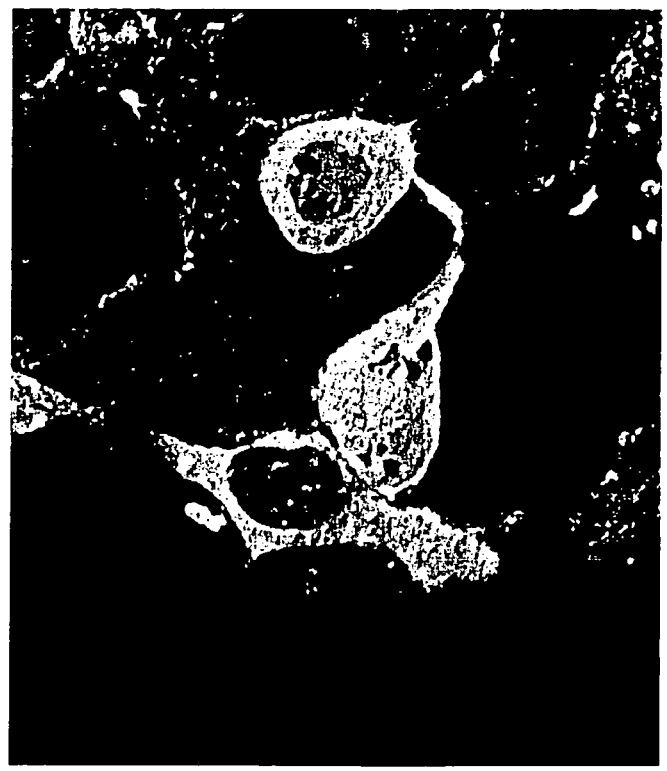
Figure 4:
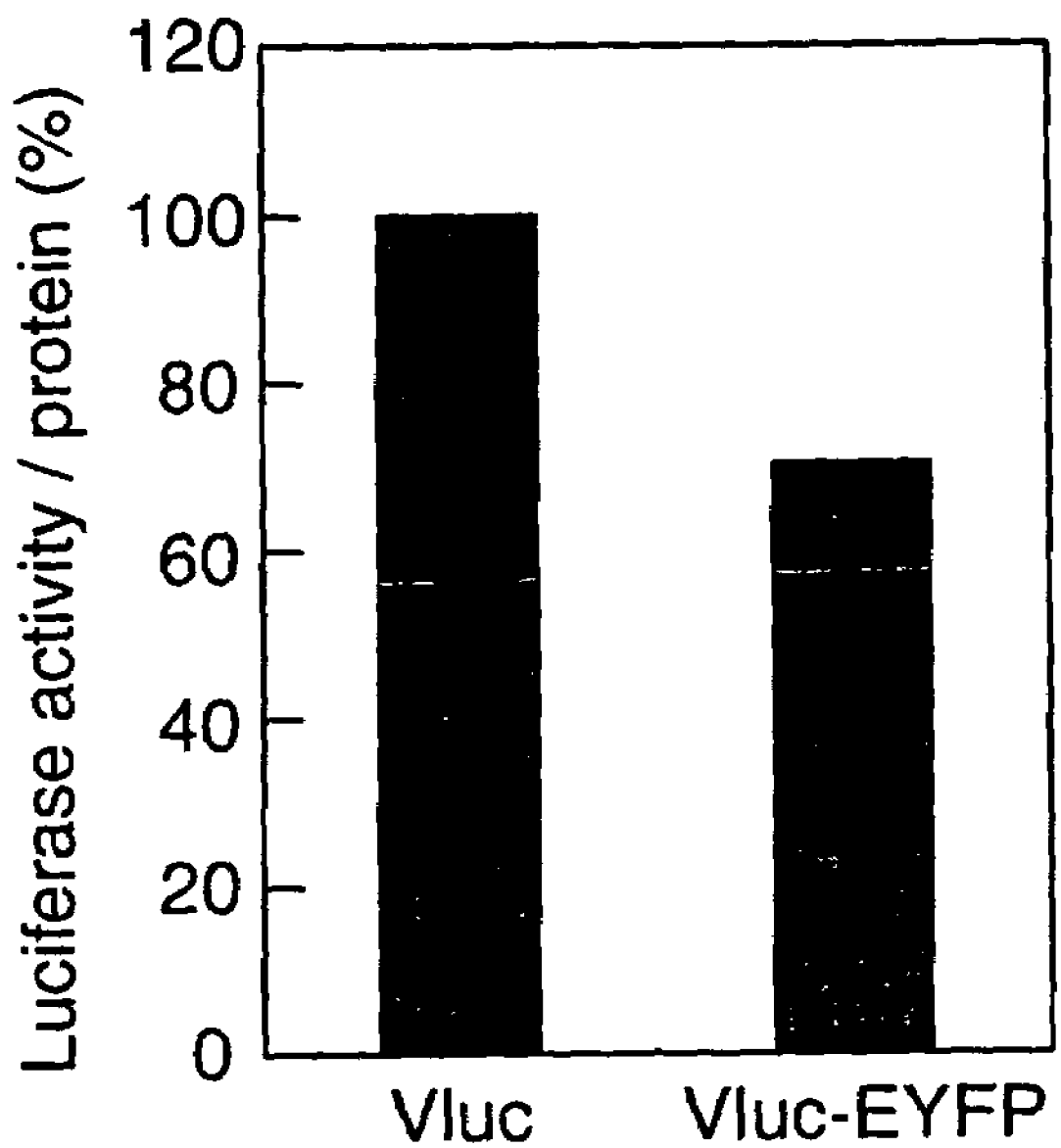
FIG. 4 shows a comparison of luminescence activities of a *Vargula* luciferase alone (Vluc) and a luminescent fluorescent fusion protein (Vluc-EYFP).

The luminescent/fluorescent fusion protein gene, pEF-BOS Vluc-EYFP was introduced into COS7 cells, and it has confirmed by Western blotting method using a light-emitting enzyme Vluc antibody and a fluorescent protein EYFP antibody that the luminescent/fluorescent fusion protein, Vluc-EYFP had been produced. FIG. 2 shows the intracellular results and the results from the extracellular medium when Vluc, EYFP and Vluc-EYFP were introduced, respectively. The Vluc (molecular weight: 63 kDa), the EYFP (27 kDa), and the Vluc-EYFP (95 kDa) were secreted out of the cells. In the intracellular expression of Vluc-EYFP, smaller size proteins were also produced whereas the secreted one appears to have a full length. Since the fusion protein is secreted, fluorescent images of the COS7 cells were observed. As a comparison, cells in which Rluc-EYFP which was a fusion of *Renilla* luciferase, Rluc with no secretory signal and EYFP had been introduced were observed. According to the fluorescent images in FIG. 3, it has been confirmed that the fluorescence of RLUC-EYFP is distributed evenly throughout the cells whereas the fluorescence of Vluc-EYFP is localized in the cells, indicating that the Vluc-EYFP protein is secreted by responding to the secretory signal of the Vluc. A luminescence activity of the secreted Vluc-EYFP was measured, and consequently the Vluc-EYFP retained about 80% luminescence activity relative to the Vluc alone as shown in FIG. 4. From the above results, it has been confirmed that the Vluc-EYFP is the fusion protein having a luminescence activity ability and a secretory ability which the Vluc has and a fluorescent ability of the fluorescent protein. The fluorescence activity, the secretory ability and the fluorescence also indicate a strength of a promoter activity, a visualization ability of a secretory process/pathway, and a localization of the fusion protein, respectively.

EXAMPLE 3

Figure 5:
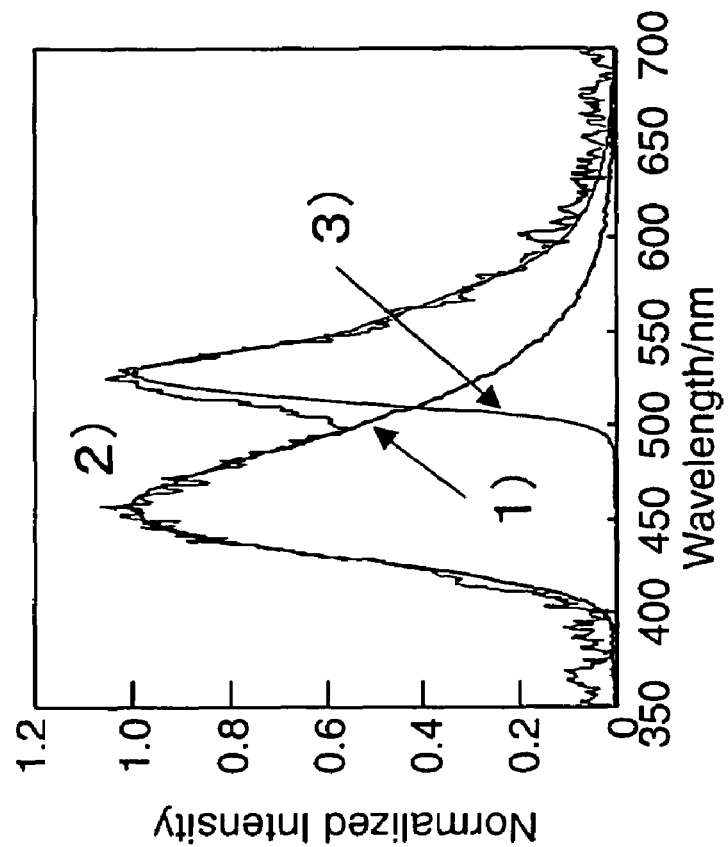
FIG. 5 shows luminescence spectra of a light-emitting enzyme alone and a light-emitting enzyme/fluorescent protein fusion. A peak obtained by energy transfer was conformed to a fluorescent spectrum of a fluorescent protein. 1) Luminescence of Vluc alone, 2) luminescence of Vluc-EYFP, and 3) luminescence of EYFP.
Figure 5:
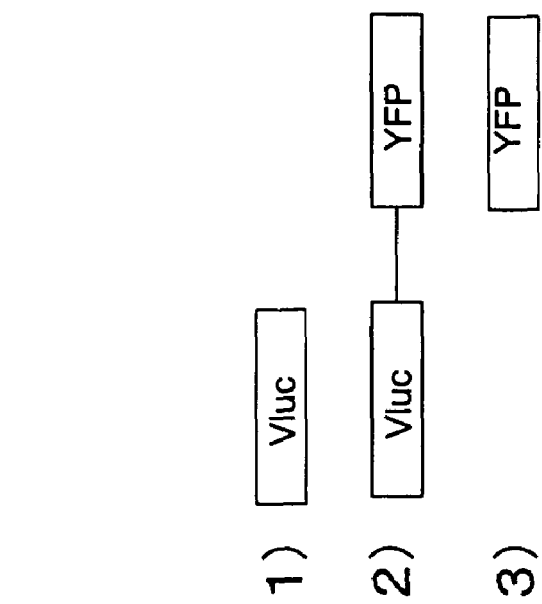

Luminescence spectra of the Vluc-EYFP were measured. Two peaks of the luminescence spectra were observed as shown in FIG. 5 (FIG. 5-2). One was conformed to a peak of the light-emitting enzyme alone (FIG. 5-1), i.e., a maximum luminescence wavelength of 460 nm. A peak at a longer wavelength side was conformed to a peak of a fluorescent spectrum of the fluorescent protein alone (FIG. 5-3), and was also conformed to a fluorescent spectrum of the light-emitting/fluorescent fusion protein. This peak at the longer wavelength side is attributed to the energy transfer between the photoprotein and the fluorescent protein, i.e., the light emitted from the photoprotein becomes excitation light, and the light with longer wavelength, fluorescence was emitted from the fluorescent protein by the excitation light. It has been confirmed that this energy transfer does not arise even when the Vluc and the EYFP are simply mixed. Therefore, the Vluc-EYFP is a construct having the secretory property, where the light-emitting/fluorescence property and the energy transfer property between the photoprotein and the fluorescent protein are retained.

EXAMPLE 4

Figure 6:
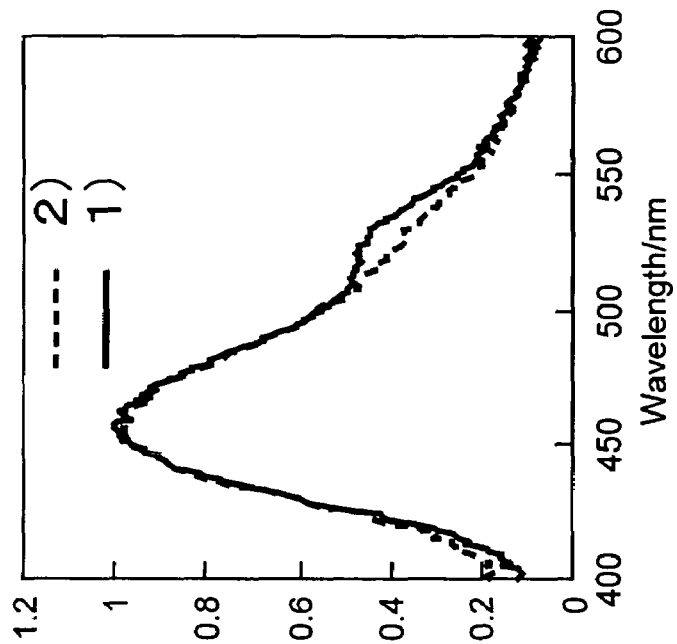
FIG. 6 shows changes of energy transfer efficiency (changes of luminescence spectra) when a different monitor peptide was inserted in a light-emitting enzyme/fluorescent protein fusion. Insert Peptide 1 (SEQ ID NO: 4) and Insert Peptide 2 (SEQ ID NO: 5) are shown.
Figure 6:
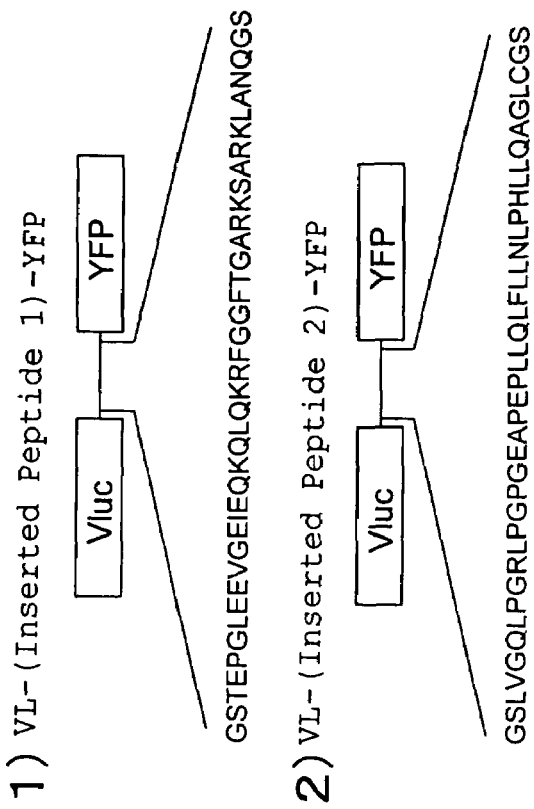
Figure 7:
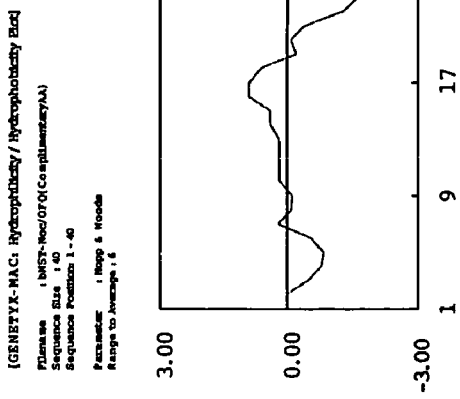
FIG. 7 shows predicted secondary structures and hydrophobicity of inserted peptides 1 (SEQ ID NO: 4) and 2 (SEQ ID NO: 5).
Figure 7:
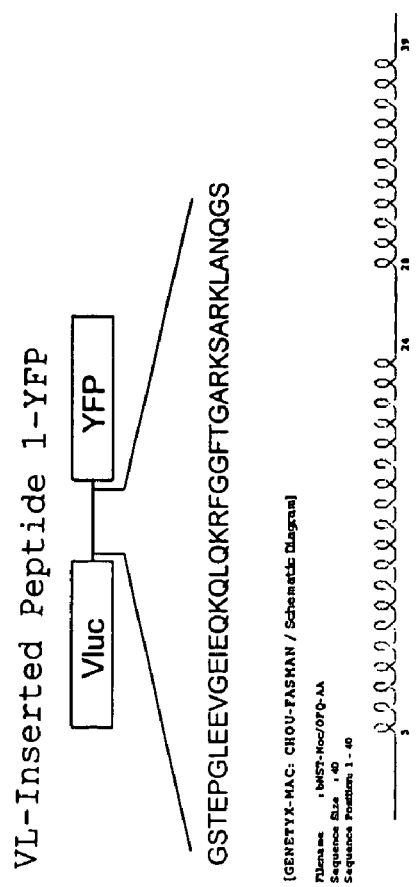
Figure 7:
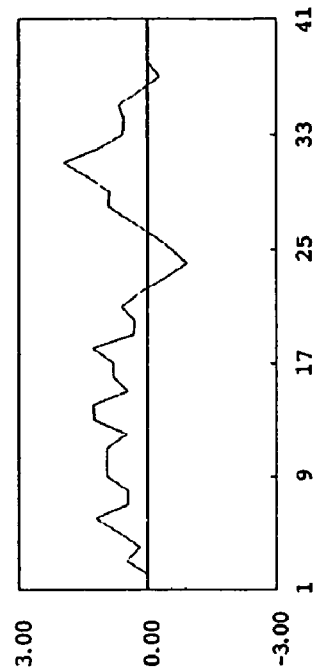
Figure 7:
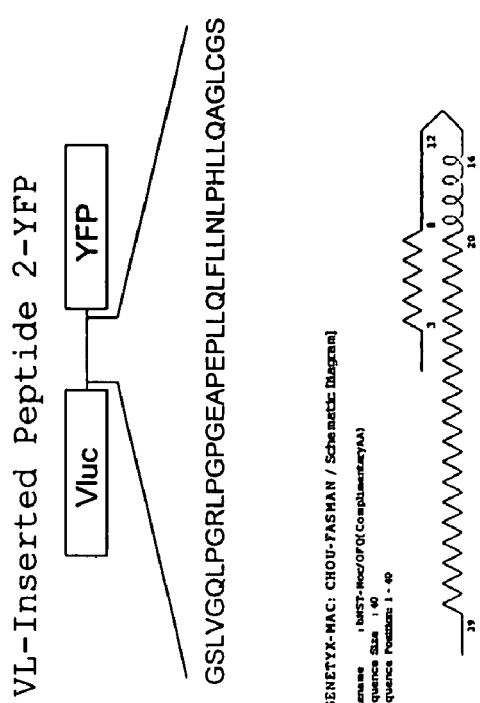

Two peptide sequences were inserted, respectively at BamHI restriction enzyme site of a linker sequence moiety of the luminescent/fluorescent fusion protein gene. FIG. 6 shows luminescence spectra for the inserted peptide 1 and the inserted peptide 2. In the protein with the inserted peptide 1, the energy transfer arose and a small peak at the longer wavelength side was observed. However, in the protein with the inserted peptide 2, no energy transfer arose. From this result, it has been demonstrated that the energy transfer depends on the inserted peptide sequence. A secondary structure of each peptide was predicted, hydrophobicity was analyzed, and consequently it was anticipated that a three dimensional structure of each peptide was different one another (FIG. 7). It has been demonstrated that three dimensional structure information of the inserted peptide can be obtained by the use of this energy transfer difference as an indicator.

The present invention provides the monitor protein, the gene encoding it, and the gene which controls the expression of the present enzyme. This fusion protein has the secretory property and biological luminescence activity of the *Vargula* luciferase and simultaneously has the fluorescence activity of the fluorescent protein. The *Vargula* luciferase-fluorescent protein fusion protein can be utilized as multiple markers for quantitatively monitoring an expressed amount of the gene and the secretion out of the cells by the enzymatic activity and a position information of secretory sites in the cells by the fluorescence. Furthermore, it can be utilized as a sensor for obtaining a functional change information of the three dimensional structure, the cleavage and the sugar addition of the inserted peptide because the energy transfer efficiency is changed by arranging the peptide between the luciferase and the fluorescent protein.

---

The invention claimed is:

1. An isolated polynucleotide comprising the sequence of SEQ ID NO: 1, said polynucleotide encodes a secretory or membrane-binding chimeric protein, wherein the chimeric protein is composed of *Vargula* luciferase and Yellow fluorescent protein (YFP).

2. A vector comprising the polynucleotide of claim 1.

3. A transformant comprising the vector of claim 2.

4. A method for producing a secretory or membrane-binding chimeric protein comprising:

(a) culturing the transformant of claim 3 in a medium; and (b) collecting the secretory or membrane-binding chimeric protein from the medium.

5. An isolated polynucleotide encoding a chimeric protein, wherein said polynucleotide comprises the sequence of SEQ ID NO:1.

* * * * *

SEQUENCE LISTING

```
<160> NUMBER OF SEQ ID NOS: 10

<210> SEQ ID NO 1
<211> LENGTH: 2388
<212> TYPE: DNA
<213> ORGANISM: Artificial Sequence
<220> FEATURE:
<223> OTHER INFORMATION: fused gene consisting of Vargula Luciferase,
      yellow fluorescence protein from Aequorea and a DNA coding for
      spacer peptide
<220> FEATURE:
<221> NAME/KEY: CDS
<222> LOCATION: (1)..(2388)
<223> OTHER INFORMATION:

<400> SEQUENCE: 1 atg aag ata ata att ctg tct gtt ata ttg gcc tac tgt gtc acc gac         48
Met Lys Ile Ile Ile Leu Ser Val Ile Leu Ala Tyr Cys Val Thr Asp
1               5                   10                  15 aac tgt caa gat gca tgt cct gta gaa gcg gaa ccg cca tca agt aca         96
Asn Cys Gln Asp Ala Cys Pro Val Glu Ala Glu Pro Pro Ser Ser Thr
            20                  25                  30 cca aca gtt cca act tct tgt gaa gct aaa gaa gga gaa tgt ata gat        144
Pro Thr Val Pro Thr Ser Cys Glu Ala Lys Glu Gly Glu Cys Ile Asp
        35                  40                  45
```

-continued

| | |
|---|---|
| acc aga tgc gca aca tgt aaa cga gat ata cta tca gat gga ctg tgt<br>Thr Arg Cys Ala Thr Cys Lys Arg Asp Ile Leu Ser Asp Gly Leu Cys<br>50                             55                             60 | 192 |
| gaa aat aaa cca ggg aag aca tgc tgt aga atg tgc cag tat gtg att<br>Glu Asn Lys Pro Gly Lys Thr Cys Cys Arg Met Cys Gln Tyr Val Ile<br>65                             70                         75                       80 | 240 |
| gaa tgc aga gta gaa gca gct ggt tat ttt aga acg ttt tac ggc aaa<br>Glu Cys Arg Val Glu Ala Ala Gly Tyr Phe Arg Thr Phe Tyr Gly Lys<br>                       85                         90                       95 | 288 |
| aga ttt aat ttt cag gaa cct ggt aaa tat gtg ctg gct agg gga acc<br>Arg Phe Asn Phe Gln Glu Pro Gly Lys Tyr Val Leu Ala Arg Gly Thr<br>                 100                      105                      110 | 336 |
| aag ggt ggc gat tgg tct gta acc ctc acc atg gag aat cta gat gga<br>Lys Gly Gly Asp Trp Ser Val Thr Leu Thr Met Glu Asn Leu Asp Gly<br>                 115                      120                      125 | 384 |
| cag aag gga gct gtg ctg act aag aca aca ctg gag gtt gca gga gac<br>Gln Lys Gly Ala Val Leu Thr Lys Thr Thr Leu Glu Val Ala Gly Asp<br>130                           135                       140 | 432 |
| gta ata gac att act caa gct act gca gat cct atc aca gtt aac gga<br>Val Ile Asp Ile Thr Gln Ala Thr Ala Asp Pro Ile Thr Val Asn Gly<br>145                           150                       155                  160 | 480 |
| gga gct gac cca gtt atc gct aac ccg ttc aca att ggt gag gtg acc<br>Gly Ala Asp Pro Val Ile Ala Asn Pro Phe Thr Ile Gly Glu Val Thr<br>                 165                      170                      175 | 528 |
| att gct gtt gtt gaa ata ccg ggc ttc aat atc aca gtc atc gaa ttc<br>Ile Ala Val Val Glu Ile Pro Gly Phe Asn Ile Thr Val Ile Glu Phe<br>                 180                      185                      190 | 576 |
| ttt aaa cta atc gtg att gat att ctg gga gga aga tct gtg aga att<br>Phe Lys Leu Ile Val Ile Asp Ile Leu Gly Gly Arg Ser Val Arg Ile<br>                 195                      200                      205 | 624 |
| gct cca gac aca gca aac aaa gga ctg ata tct ggt atc tgt ggt aat<br>Ala Pro Asp Thr Ala Asn Lys Gly Leu Ile Ser Gly Ile Cys Gly Asn<br>210                           215                       220 | 672 |
| ctg gag atg aat gac gct gat gac ttt act aca gat gca gat cag ctg<br>Leu Glu Met Asn Asp Ala Asp Asp Phe Thr Thr Asp Ala Asp Gln Leu<br>225                           230                       235                  240 | 720 |
| gcg atc caa ccc aac ata aac aaa gag ttc gac ggc tgc cca ttc tat<br>Ala Ile Gln Pro Asn Ile Asn Lys Glu Phe Asp Gly Cys Pro Phe Tyr<br>                               245                      250                      255 | 768 |
| ggc aat cct tct gat atc gaa tac tgc aaa ggt ctg atg gag cca tac<br>Gly Asn Pro Ser Asp Ile Glu Tyr Cys Lys Gly Leu Met Glu Pro Tyr<br>                 260                      265                      270 | 816 |
| aga gct gta tgt cgt aac aat atc aac ttc tac tat tac act cta tcc<br>Arg Ala Val Cys Arg Asn Asn Ile Asn Phe Tyr Tyr Tyr Thr Leu Ser<br>                 275                      280                      285 | 864 |
| tgt gcc ttc gct tac tgt atg gga gga gaa gaa aga gct aaa cac gtc<br>Cys Ala Phe Ala Tyr Cys Met Gly Gly Glu Glu Arg Ala Lys His Val<br>290                           295                       300 | 912 |
| ctt ttc gac tat gtt gag aca tgc gct gcg ccg gaa acg aga gga acg<br>Leu Phe Asp Tyr Val Glu Thr Cys Ala Ala Pro Glu Thr Arg Gly Thr<br>305                           310                       315                  320 | 960 |
| tgt gtt tta tca gga cat act ttc tat gac aca ttc gac aaa gca aga<br>Cys Val Leu Ser Gly His Thr Phe Tyr Asp Thr Phe Asp Lys Ala Arg<br>                 325                      330                      335 | 1008 |
| tat caa ttc cag ggc cca tgc aag gag att ctg atg gcc gca gac tgt<br>Tyr Gln Phe Gln Gly Pro Cys Lys Glu Ile Leu Met Ala Ala Asp Cys<br>                 340                      345                      350 | 1056 |
| tac tgg aac aca tgg gat gta aag gtt tca cat aga gac gtc gaa tca<br>Tyr Trp Asn Thr Trp Asp Val Lys Val Ser His Arg Asp Val Glu Ser | 1104 |

```
                    355                 360                 365
tac act gag gta gag aaa gta aca atc agg aaa cag tca act gta gta    1152
Tyr Thr Glu Val Glu Lys Val Thr Ile Arg Lys Gln Ser Thr Val Val
        370                 375                 380 gat ctc att gtg gat ggc aag cag gtc aag gtt gga gga gtg gat gta    1200
Asp Leu Ile Val Asp Gly Lys Gln Val Lys Val Gly Gly Val Asp Val
385                 390                 395                 400 tct atc ccg tac agc tct gag aac act tcc ata tac tgg cag gat gga    1248
Ser Ile Pro Tyr Ser Ser Glu Asn Thr Ser Ile Tyr Trp Gln Asp Gly
                405                 410                 415 gac atc ctg acg acg gcc atc cta cct gaa gct ctt gtc gtt aag ttc    1296
Asp Ile Leu Thr Thr Ala Ile Leu Pro Glu Ala Leu Val Val Lys Phe
            420                 425                 430 aac ttt aag cag ctc ctt gta gtt cat atc aga gat cca ttc gat gga    1344
Asn Phe Lys Gln Leu Leu Val Val His Ile Arg Asp Pro Phe Asp Gly
        435                 440                 445 aag aca tgc ggc ata tgt ggt aac tat aat caa gat tca act gat gat    1392
Lys Thr Cys Gly Ile Cys Gly Asn Tyr Asn Gln Asp Ser Thr Asp Asp
450                 455                 460 ttc ttt gac gca gaa gga gca tgc gct cta acc ccc aac ccc cca gga    1440
Phe Phe Asp Ala Glu Gly Ala Cys Ala Leu Thr Pro Asn Pro Pro Gly
465                 470                 475                 480 tgt aca gag gaa cag aaa cca gaa gct gag cga ctt tgc aat aat ctc    1488
Cys Thr Glu Glu Gln Lys Pro Glu Ala Glu Arg Leu Cys Asn Asn Leu
                485                 490                 495 ttt gat tct tct atc gac gag aaa tgt aat gtc tgc tac aag cct gac    1536
Phe Asp Ser Ser Ile Asp Glu Lys Cys Asn Val Cys Tyr Lys Pro Asp
            500                 505                 510 cgg att gcc cga tgt atg tac gag tat tgc ctg agg gga caa caa gga    1584
Arg Ile Ala Arg Cys Met Tyr Glu Tyr Cys Leu Arg Gly Gln Gln Gly
        515                 520                 525 ttt tgt gac cat gct tgg gag ttc aag aaa gaa tgc tac ata aaa cat    1632
Phe Cys Asp His Ala Trp Glu Phe Lys Lys Glu Cys Tyr Ile Lys His
530                 535                 540 gga gac act cta gaa gta cca cct gaa tgt caa gga tcc gtg agc aag    1680
Gly Asp Thr Leu Glu Val Pro Pro Glu Cys Gln Gly Ser Val Ser Lys
545                 550                 555                 560 ggc gag gag ctg ttc acc ggg gtg gtg ccc atc ctg gtc gag ctg gac    1728
Gly Glu Glu Leu Phe Thr Gly Val Val Pro Ile Leu Val Glu Leu Asp
                565                 570                 575 ggc gac gta aac ggc cac aag ttc agc gtg tcc ggc gag ggc gag ggc    1776
Gly Asp Val Asn Gly His Lys Phe Ser Val Ser Gly Glu Gly Glu Gly
            580                 585                 590 gat gcc acc tac ggc aag ctg acc ctg aag ttc atc tgc acc acc ggc    1824
Asp Ala Thr Tyr Gly Lys Leu Thr Leu Lys Phe Ile Cys Thr Thr Gly
        595                 600                 605 aag ctg ccc gtg ccc tgg ccc acc ctc gtg acc acc ttc ggc tac ggc    1872
Lys Leu Pro Val Pro Trp Pro Thr Leu Val Thr Thr Phe Gly Tyr Gly
610                 615                 620 ctg cag tgc ttc gcc cgc tac ccc gac cac atg aag cag cac gac ttc    1920
Leu Gln Cys Phe Ala Arg Tyr Pro Asp His Met Lys Gln His Asp Phe
625                 630                 635                 640 ttc aag tcc gcc atg ccc gaa ggc tac gtc cag gag cgc acc atc ttc    1968
Phe Lys Ser Ala Met Pro Glu Gly Tyr Val Gln Glu Arg Thr Ile Phe
                645                 650                 655 ttc aag gac gac ggc aac tac aag acc cgc gcc gag gtg aag ttc gag    2016
Phe Lys Asp Asp Gly Asn Tyr Lys Thr Arg Ala Glu Val Lys Phe Glu
            660                 665                 670 ggc gac acc ctg gtg aac cgc atc gag ctg aag ggc atc gac ttc aag    2064
```

```
                Gly Asp Thr Leu Val Asn Arg Ile Glu Leu Lys Gly Ile Asp Phe Lys
                            675                 680                 685 gag gac ggc aac atc ctg ggg cac aag ctg gag tac aac tac aac agc        2112
Glu Asp Gly Asn Ile Leu Gly His Lys Leu Glu Tyr Asn Tyr Asn Ser
        690                 695                 700 cac aac gtc tat atc atg gcc gac aag cag aag aac ggc atc aag gtg        2160
His Asn Val Tyr Ile Met Ala Asp Lys Gln Lys Asn Gly Ile Lys Val
705                 710                 715                 720 aac ttc aag atc cgc cac aac atc gag gac ggc agc gtg cag ctc gcc        2208
Asn Phe Lys Ile Arg His Asn Ile Glu Asp Gly Ser Val Gln Leu Ala
                725                 730                 735 gac cac tac cag cag aac acc ccc atc ggc gac ggc ccc gtg ctg ctg        2256
Asp His Tyr Gln Gln Asn Thr Pro Ile Gly Asp Gly Pro Val Leu Leu
            740                 745                 750 ccc gac aac cac tac ctg agc tac cag tcc gcc ctg agc aaa gac ccc        2304
Pro Asp Asn His Tyr Leu Ser Tyr Gln Ser Ala Leu Ser Lys Asp Pro
        755                 760                 765 aac gag aag cgc gat cac atg gtc ctg ctg gag ttc gtg acc gcc gcc        2352
Asn Glu Lys Arg Asp His Met Val Leu Leu Glu Phe Val Thr Ala Ala
    770                 775                 780 ggg atc act ctc ggc atg gac gag ctg tac aag taa                        2388
Gly Ile Thr Leu Gly Met Asp Glu Leu Tyr Lys
785                 790                 795

<210> SEQ ID NO 2
<211> LENGTH: 2502
<212> TYPE: DNA
<213> ORGANISM: Artificial Sequence
<220> FEATURE:
<221> NAME/KEY: CDS
<222> LOCATION: (1)..(2502)
<223> OTHER INFORMATION: chimeric protein

<400> SEQUENCE: 2 atg aag ata ata att ctg tct gtt ata ttg gcc tac tgt gtc acc gac         48
Met Lys Ile Ile Ile Leu Ser Val Ile Leu Ala Tyr Cys Val Thr Asp
1               5                   10                  15 aac tgt caa gat gca tgt cct gta gaa gcg gaa ccg cca tca agt aca         96
Asn Cys Gln Asp Ala Cys Pro Val Glu Ala Glu Pro Pro Ser Ser Thr
                20                  25                  30 cca aca gtt cca act tct tgt gaa gct aaa gaa gga gaa tgt ata gat        144
Pro Thr Val Pro Thr Ser Cys Glu Ala Lys Glu Gly Glu Cys Ile Asp
            35                  40                  45 acc aga tgc gca aca tgt aaa cga gat ata cta tca gat gga ctg tgt        192
Thr Arg Cys Ala Thr Cys Lys Arg Asp Ile Leu Ser Asp Gly Leu Cys
        50                  55                  60 gaa aat aaa cca ggg aag aca tgc tgt aga atg tgc cag tat gtg att        240
Glu Asn Lys Pro Gly Lys Thr Cys Cys Arg Met Cys Gln Tyr Val Ile
65                  70                  75                  80 gaa tgc aga gta gaa gca gct ggt tat ttt aga acg ttt tac ggc aaa        288
Glu Cys Arg Val Glu Ala Ala Gly Tyr Phe Arg Thr Phe Tyr Gly Lys
                85                  90                  95 aga ttt aat ttt cag gaa cct ggt aaa tat gtg ctg gct agg gga acc        336
Arg Phe Asn Phe Gln Glu Pro Gly Lys Tyr Val Leu Ala Arg Gly Thr
            100                 105                 110 aag ggt ggc gat tgg tct gta acc ctc acc atg gag aat cta gat gga        384
Lys Gly Gly Asp Trp Ser Val Thr Leu Thr Met Glu Asn Leu Asp Gly
        115                 120                 125 cag aag gga gct gtg ctg act aag aca aca ctg gag gtt gca gga gac        432
Gln Lys Gly Ala Val Leu Thr Lys Thr Thr Leu Glu Val Ala Gly Asp
    130                 135                 140
```

```
                          -continued
gta ata gac att act caa gct act gca gat cct atc aca gtt aac gga      480
Val Ile Asp Ile Thr Gln Ala Thr Ala Asp Pro Ile Thr Val Asn Gly
145                 150                 155                 160 gga gct gac cca gtt atc gct aac ccg ttc aca att ggt gag gtg acc      528
Gly Ala Asp Pro Val Ile Ala Asn Pro Phe Thr Ile Gly Glu Val Thr
                165                 170                 175 att gct gtt gtt gaa ata ccg ggc ttc aat atc aca gtc atc gaa ttc      576
Ile Ala Val Val Glu Ile Pro Gly Phe Asn Ile Thr Val Ile Glu Phe
            180                 185                 190 ttt aaa cta atc gtg att gat att ctg gga gga aga tct gtg aga att      624
Phe Lys Leu Ile Val Ile Asp Ile Leu Gly Gly Arg Ser Val Arg Ile
        195                 200                 205 gct cca gac aca gca aac aaa gga ctg ata tct ggt atc tgt ggt aat      672
Ala Pro Asp Thr Ala Asn Lys Gly Leu Ile Ser Gly Ile Cys Gly Asn
    210                 215                 220 ctg gag atg aat gac gct gat gac ttt act aca gat gca gat cag ctg      720
Leu Glu Met Asn Asp Ala Asp Asp Phe Thr Thr Asp Ala Asp Gln Leu
225                 230                 235                 240 gcg atc caa ccc aac ata aac aaa gag ttc gac ggc tgc cca ttc tat      768
Ala Ile Gln Pro Asn Ile Asn Lys Glu Phe Asp Gly Cys Pro Phe Tyr
                245                 250                 255 ggc aat cct tct gat atc gaa tac tgc aaa ggt ctg atg gag cca tac      816
Gly Asn Pro Ser Asp Ile Glu Tyr Cys Lys Gly Leu Met Glu Pro Tyr
            260                 265                 270 aga gct gta tgt cgt aac aat atc aac ttc tac tat tac act cta tcc      864
Arg Ala Val Cys Arg Asn Asn Ile Asn Phe Tyr Tyr Tyr Thr Leu Ser
        275                 280                 285 tgt gcc ttc gct tac tgt atg gga gga gaa gaa aga gct aaa cac gtc      912
Cys Ala Phe Ala Tyr Cys Met Gly Gly Glu Glu Arg Ala Lys His Val
    290                 295                 300 ctt ttc gac tat gtt gag aca tgc gct gcg ccg gaa acg aga gga acg      960
Leu Phe Asp Tyr Val Glu Thr Cys Ala Ala Pro Glu Thr Arg Gly Thr
305                 310                 315                 320 tgt gtt tta tca gga cat act ttc tat gac aca ttc gac aaa gca aga     1008
Cys Val Leu Ser Gly His Thr Phe Tyr Asp Thr Phe Asp Lys Ala Arg
                325                 330                 335 tat caa ttc cag ggc cca tgc aag gag att ctg atg gcc gca gac tgt     1056
Tyr Gln Phe Gln Gly Pro Cys Lys Glu Ile Leu Met Ala Ala Asp Cys
            340                 345                 350 tac tgg aac aca tgg gat gta aag gtt tca cat aga gac gtc gaa tca     1104
Tyr Trp Asn Thr Trp Asp Val Lys Val Ser His Arg Asp Val Glu Ser
        355                 360                 365 tac act gag gta gag aaa gta aca atc agg aaa cag tca act gta gta     1152
Tyr Thr Glu Val Glu Lys Val Thr Ile Arg Lys Gln Ser Thr Val Val
    370                 375                 380 gat ctc att gtg gat ggc aag cag gtc aag gtt gga gga gtg gat gta     1200
Asp Leu Ile Val Asp Gly Lys Gln Val Lys Val Gly Gly Val Asp Val
385                 390                 395                 400 tct atc ccg tac agc tct gag aac act tcc ata tac tgg cag gat gga     1248
Ser Ile Pro Tyr Ser Ser Glu Asn Thr Ser Ile Tyr Trp Gln Asp Gly
                405                 410                 415 gac atc ctg acg acg gcc atc cta cct gaa gct ctt gtc gtt aag ttc     1296
Asp Ile Leu Thr Thr Ala Ile Leu Pro Glu Ala Leu Val Val Lys Phe
            420                 425                 430 aac ttt aag cag ctc ctt gta gtt cat atc aga gat cca ttc gat gga     1344
Asn Phe Lys Gln Leu Leu Val Val His Ile Arg Asp Pro Phe Asp Gly
        435                 440                 445 aag aca tgc ggc ata tgt ggt aac tat aat caa gat tca act gat gat     1392
Lys Thr Cys Gly Ile Cys Gly Asn Tyr Asn Gln Asp Ser Thr Asp Asp
    450                 455                 460
```

-continued

```
ttc ttt gac gca gaa gga gca tgc gct cta acc ccc aac ccc cca gga     1440
Phe Phe Asp Ala Glu Gly Ala Cys Ala Leu Thr Pro Asn Pro Pro Gly
465                 470                 475                 480 tgt aca gag gaa cag aaa cca gaa gct gag cga ctt tgc aat aat ctc     1488
Cys Thr Glu Glu Gln Lys Pro Glu Ala Glu Arg Leu Cys Asn Asn Leu
                485                 490                 495 ttt gat tct tct atc gac gag aaa tgt aat gtc tgc tac aag cct gac     1536
Phe Asp Ser Ser Ile Asp Glu Lys Cys Asn Val Cys Tyr Lys Pro Asp
                500                 505                 510 cgg att gcc cga tgt atg tac gag tat tgc ctg agg gga caa caa gga     1584
Arg Ile Ala Arg Cys Met Tyr Glu Tyr Cys Leu Arg Gly Gln Gln Gly
        515                 520                 525 ttt tgt gac cat gct tgg gag ttc aag aaa gaa tgc tac ata aaa cat     1632
Phe Cys Asp His Ala Trp Glu Phe Lys Lys Glu Cys Tyr Ile Lys His
530                 535                 540 gga gac act cta gaa gta cca cct gaa tgt caa gga tcc aca gag ccc     1680
Gly Asp Thr Leu Glu Val Pro Pro Glu Cys Gln Gly Ser Thr Glu Pro
545                 550                 555                 560 ggc ctg gag gag gtg ggg gag att gag cag aaa cag ctg cag aag cgg     1728
Gly Leu Glu Glu Val Gly Glu Ile Glu Gln Lys Gln Leu Gln Lys Arg
                565                 570                 575 ttc ggg ggc ttc acc ggg gcc cgg aag tcg gcc cgg aag ttg gcc aac     1776
Phe Gly Gly Phe Thr Gly Ala Arg Lys Ser Ala Arg Lys Leu Ala Asn
                580                 585                 590 cag gga tcc gtg agc aag ggc gag gag ctg ttc acc ggg gtg gtg ccc     1824
Gln Gly Ser Val Ser Lys Gly Glu Glu Leu Phe Thr Gly Val Val Pro
                595                 600                 605 atc ctg gtc gag ctg gac ggc gac gta aac ggc cac aag ttc agc gtg     1872
Ile Leu Val Glu Leu Asp Gly Asp Val Asn Gly His Lys Phe Ser Val
610                 615                 620 tcc ggc gag ggc gag ggc gat gcc acc tac ggc aag ctg acc ctg aag     1920
Ser Gly Glu Gly Glu Gly Asp Ala Thr Tyr Gly Lys Leu Thr Leu Lys
625                 630                 635                 640 ttc atc tgc acc acc ggc aag ctg ccc gtg ccc tgg ccc acc ctc gtg     1968
Phe Ile Cys Thr Thr Gly Lys Leu Pro Val Pro Trp Pro Thr Leu Val
                645                 650                 655 acc acc ttc ggc tac ggc ctg cag tgc ttc gcc cgc tac ccc gac cac     2016
Thr Thr Phe Gly Tyr Gly Leu Gln Cys Phe Ala Arg Tyr Pro Asp His
                660                 665                 670 atg aag cag cac gac ttc ttc aag tcc gcc atg ccc gaa ggc tac gtc     2064
Met Lys Gln His Asp Phe Phe Lys Ser Ala Met Pro Glu Gly Tyr Val
                675                 680                 685 cag gag cgc acc atc ttc ttc aag gac gac ggc aac tac aag acc cgc     2112
Gln Glu Arg Thr Ile Phe Phe Lys Asp Asp Gly Asn Tyr Lys Thr Arg
                690                 695                 700 gcc gag gtg aag ttc gag ggc gac acc ctg gtg aac cgc atc gag ctg     2160
Ala Glu Val Lys Phe Glu Gly Asp Thr Leu Val Asn Arg Ile Glu Leu
705                 710                 715                 720 aag ggc atc gac ttc aag gag gac ggc aac atc ctg ggg cac aag ctg     2208
Lys Gly Ile Asp Phe Lys Glu Asp Gly Asn Ile Leu Gly His Lys Leu
                725                 730                 735 gag tac aac tac aac agc cac aac gtc tat atc atg gcc gac aag cag     2256
Glu Tyr Asn Tyr Asn Ser His Asn Val Tyr Ile Met Ala Asp Lys Gln
                740                 745                 750 aag aac ggc atc aag gtg aac ttc aag atc cgc cac aac atc gag gac     2304
Lys Asn Gly Ile Lys Val Asn Phe Lys Ile Arg His Asn Ile Glu Asp
                755                 760                 765 ggc agc gtg cag ctc gcc gac cac tac cag cag aac acc ccc atc ggc     2352
Gly Ser Val Gln Leu Ala Asp His Tyr Gln Gln Asn Thr Pro Ile Gly
```

```
                770             775             780
gac ggc ccc gtg ctg ctg ccc gac aac cac tac ctg agc tac cag tcc    2400
Asp Gly Pro Val Leu Leu Pro Asp Asn His Tyr Leu Ser Tyr Gln Ser
785                 790                 795                 800 gcc ctg agc aaa gac ccc aac gag aag cgc gat cac atg gtc ctg ctg    2448
Ala Leu Ser Lys Asp Pro Asn Glu Lys Arg Asp His Met Val Leu Leu
                805                 810                 815 gag ttc gtg acc gcc gcc ggg atc act ctc ggc atg gac gag ctg tac    2496
Glu Phe Val Thr Ala Ala Gly Ile Thr Leu Gly Met Asp Glu Leu Tyr
            820                 825                 830 aag taa                                                            2502
Lys

<210> SEQ ID NO 3
<211> LENGTH: 2502
<212> TYPE: DNA
<213> ORGANISM: Artificial Sequence
<220> FEATURE:
<221> NAME/KEY: CDS
<222> LOCATION: (1)..(2502)
<223> OTHER INFORMATION: chimeric protein

<400> SEQUENCE: 3 atg aag ata ata att ctg tct gtt ata ttg gcc tac tgt gtc acc gac      48
Met Lys Ile Ile Ile Leu Ser Val Ile Leu Ala Tyr Cys Val Thr Asp
1               5                   10                  15 aac tgt caa gat gca tgt cct gta gaa gcg gaa ccg cca tca agt aca      96
Asn Cys Gln Asp Ala Cys Pro Val Glu Ala Glu Pro Pro Ser Ser Thr
                20                  25                  30 cca aca gtt cca act tct tgt gaa gct aaa gaa gga gaa tgt ata gat     144
Pro Thr Val Pro Thr Ser Cys Glu Ala Lys Glu Gly Glu Cys Ile Asp
            35                  40                  45 acc aga tgc gca aca tgt aaa cga gat ata cta tca gat gga ctg tgt     192
Thr Arg Cys Ala Thr Cys Lys Arg Asp Ile Leu Ser Asp Gly Leu Cys
        50                  55                  60 gaa aat aaa cca ggg aag aca tgc tgt aga atg tgc cag tat gtg att     240
Glu Asn Lys Pro Gly Lys Thr Cys Cys Arg Met Cys Gln Tyr Val Ile
65                  70                  75                  80 gaa tgc aga gta gaa gca gct ggt tat ttt aga acg ttt tac ggc aaa     288
Glu Cys Arg Val Glu Ala Ala Gly Tyr Phe Arg Thr Phe Tyr Gly Lys
                85                  90                  95 aga ttt aat ttt cag gaa cct ggt aaa tat gtg ctg gct agg gga acc     336
Arg Phe Asn Phe Gln Glu Pro Gly Lys Tyr Val Leu Ala Arg Gly Thr
                100                 105                 110 aag ggt ggc gat tgg tct gta acc ctc acc atg gag aat cta gat gga     384
Lys Gly Gly Asp Trp Ser Val Thr Leu Thr Met Glu Asn Leu Asp Gly
            115                 120                 125 cag aag gga gct gtg ctg act aag aca aca ctg gag gtt gca gga gac     432
Gln Lys Gly Ala Val Leu Thr Lys Thr Thr Leu Glu Val Ala Gly Asp
        130                 135                 140 gta ata gac att act caa gct act gca gat cct atc aca gtt aac gga     480
Val Ile Asp Ile Thr Gln Ala Thr Ala Asp Pro Ile Thr Val Asn Gly
145                 150                 155                 160 gga gct gac cca gtt atc gct aac ccg ttc aca att ggt gag gtg acc     528
Gly Ala Asp Pro Val Ile Ala Asn Pro Phe Thr Ile Gly Glu Val Thr
                165                 170                 175 att gct gtt gtt gaa ata ccg ggc ttc aat atc aca gtc atc gaa ttc     576
Ile Ala Val Val Glu Ile Pro Gly Phe Asn Ile Thr Val Ile Glu Phe
                180                 185                 190 ttt aaa cta atc gtg att gat att ctg gga gga aga tct gtg aga att     624
Phe Lys Leu Ile Val Ile Asp Ile Leu Gly Gly Arg Ser Val Arg Ile
```

-continued

| | | | | | | | | | | | | | | | |
|---|---|---|---|---|---|---|---|---|---|---|---|---|---|---|---|
| | | 195 | | | | 200 | | | | | 205 | | | | |

```
gct cca gac aca gca aac aaa gga ctg ata tct ggt atc tgt ggt aat     672
Ala Pro Asp Thr Ala Asn Lys Gly Leu Ile Ser Gly Ile Cys Gly Asn
    210                 215                 220 ctg gag atg aat gac gct gat gac ttt act aca gat gca gat cag ctg     720
Leu Glu Met Asn Asp Ala Asp Asp Phe Thr Thr Asp Ala Asp Gln Leu
225                 230                 235                 240 gcg atc caa ccc aac ata aac aaa gag ttc gac ggc tgc cca ttc tat     768
Ala Ile Gln Pro Asn Ile Asn Lys Glu Phe Asp Gly Cys Pro Phe Tyr
                245                 250                 255 ggc aat cct tct gat atc gaa tac tgc aaa ggt ctg atg gag cca tac     816
Gly Asn Pro Ser Asp Ile Glu Tyr Cys Lys Gly Leu Met Glu Pro Tyr
            260                 265                 270 aga gct gta tgt cgt aac aat atc aac ttc tac tat tac act cta tcc     864
Arg Ala Val Cys Arg Asn Asn Ile Asn Phe Tyr Tyr Tyr Thr Leu Ser
        275                 280                 285 tgt gcc ttc gct tac tgt atg gga gga gaa gaa aga gct aaa cac gtc     912
Cys Ala Phe Ala Tyr Cys Met Gly Gly Glu Glu Arg Ala Lys His Val
    290                 295                 300 ctt ttc gac tat gtt gag aca tgc gct gcg ccg gaa acg aga gga acg     960
Leu Phe Asp Tyr Val Glu Thr Cys Ala Ala Pro Glu Thr Arg Gly Thr
305                 310                 315                 320 tgt gtt tta tca gga cat act ttc tat gac aca ttc gac aaa gca aga    1008
Cys Val Leu Ser Gly His Thr Phe Tyr Asp Thr Phe Asp Lys Ala Arg
                325                 330                 335 tat caa ttc cag ggc cca tgc aag gag att ctg atg gcc gca gac tgt    1056
Tyr Gln Phe Gln Gly Pro Cys Lys Glu Ile Leu Met Ala Ala Asp Cys
            340                 345                 350 tac tgg aac aca tgg gat gta aag gtt tca cat aga gac gtc gaa tca    1104
Tyr Trp Asn Thr Trp Asp Val Lys Val Ser His Arg Asp Val Glu Ser
        355                 360                 365 tac act gag gta gag aaa gta aca atc agg aaa cag tca act gta gta    1152
Tyr Thr Glu Val Glu Lys Val Thr Ile Arg Lys Gln Ser Thr Val Val
    370                 375                 380 gat ctc att gtg gat ggc aag cag gtc aag gtt gga gga gtg gat gta    1200
Asp Leu Ile Val Asp Gly Lys Gln Val Lys Val Gly Gly Val Asp Val
385                 390                 395                 400 tct atc ccg tac agc tct gag aac act tcc ata tac tgg cag gat gga    1248
Ser Ile Pro Tyr Ser Ser Glu Asn Thr Ser Ile Tyr Trp Gln Asp Gly
                405                 410                 415 gac atc ctg acg acg gcc atc cta cct gaa gct ctt gtc gtt aag ttc    1296
Asp Ile Leu Thr Thr Ala Ile Leu Pro Glu Ala Leu Val Val Lys Phe
            420                 425                 430 aac ttt aag cag ctc ctt gta gtt cat atc aga gat cca ttc gat gga    1344
Asn Phe Lys Gln Leu Leu Val Val His Ile Arg Asp Pro Phe Asp Gly
        435                 440                 445 aag aca tgc ggc ata tgt ggt aac tat aat caa gat tca act gat gat    1392
Lys Thr Cys Gly Ile Cys Gly Asn Tyr Asn Gln Asp Ser Thr Asp Asp
    450                 455                 460 ttc ttt gac gca gaa gga gca tgc gct cta acc ccc aac ccc cca gga    1440
Phe Phe Asp Ala Glu Gly Ala Cys Ala Leu Thr Pro Asn Pro Pro Gly
465                 470                 475                 480 tgt aca gag gaa cag aaa cca gaa gct gag cga ctt tgc aat aat ctc    1488
Cys Thr Glu Glu Gln Lys Pro Glu Ala Glu Arg Leu Cys Asn Asn Leu
                485                 490                 495 ttt gat tct tct atc gac gag aaa tgt aat gtc tgc tac aag cct gac    1536
Phe Asp Ser Ser Ile Asp Glu Lys Cys Asn Val Cys Tyr Lys Pro Asp
            500                 505                 510 cgg att gcc cga tgt atg tac gag tat tgc ctg agg gga caa caa gga    1584
```

```
                Arg Ile Ala Arg Cys Met Tyr Glu Tyr Cys Leu Arg Gly Gln Gln Gly
                        515                 520                 525 ttt tgt gac cat gct tgg gag ttc aag aaa gaa tgc tac ata aaa cat       1632
Phe Cys Asp His Ala Trp Glu Phe Lys Lys Glu Cys Tyr Ile Lys His
530                 535                 540 gga gac act cta gaa gta cca cct gaa tgt caa gga tcc ctg gtt ggc       1680
Gly Asp Thr Leu Glu Val Pro Pro Glu Cys Gln Gly Ser Leu Val Gly
545                 550                 555                 560 caa ctt ccg ggc cga ctt ccg ggc ccc ggt gaa gcc ccc gaa ccg ctt       1728
Gln Leu Pro Gly Arg Leu Pro Gly Pro Gly Glu Ala Pro Glu Pro Leu
                565                 570                 575 ctg cag ctg ttt ctg ctc aat ctc ccc cac ctc ctc cag gcc ggg ctc       1776
Leu Gln Leu Phe Leu Leu Asn Leu Pro His Leu Leu Gln Ala Gly Leu
                580                 585                 590 tgt gga tcc gtg agc aag ggc gag gag ctg ttc acc ggg gtg gtg ccc       1824
Cys Gly Ser Val Ser Lys Gly Glu Glu Leu Phe Thr Gly Val Val Pro
            595                 600                 605 atc ctg gtc gag ctg gac ggc gac gta aac ggc cac aag ttc agc gtg       1872
Ile Leu Val Glu Leu Asp Gly Asp Val Asn Gly His Lys Phe Ser Val
610                 615                 620 tcc ggc gag ggc gag ggc gat gcc acc tac ggc aag ctg acc ctg aag       1920
Ser Gly Glu Gly Glu Gly Asp Ala Thr Tyr Gly Lys Leu Thr Leu Lys
625                 630                 635                 640 ttc atc tgc acc acc ggc aag ctg ccc gtg ccc tgg ccc acc ctc gtg       1968
Phe Ile Cys Thr Thr Gly Lys Leu Pro Val Pro Trp Pro Thr Leu Val
                645                 650                 655 acc acc ttc ggc tac ggc ctg cag tgc ttc gcc cgc tac ccc gac cac       2016
Thr Thr Phe Gly Tyr Gly Leu Gln Cys Phe Ala Arg Tyr Pro Asp His
                660                 665                 670 atg aag cag cac gac ttc ttc aag tcc gcc atg ccc gaa ggc tac gtc       2064
Met Lys Gln His Asp Phe Phe Lys Ser Ala Met Pro Glu Gly Tyr Val
            675                 680                 685 cag gag cgc acc atc ttc ttc aag gac gac ggc aac tac aag acc cgc       2112
Gln Glu Arg Thr Ile Phe Phe Lys Asp Asp Gly Asn Tyr Lys Thr Arg
            690                 695                 700 gcc gag gtg aag ttc gag ggc gac acc ctg gtg aac cgc atc gag ctg       2160
Ala Glu Val Lys Phe Glu Gly Asp Thr Leu Val Asn Arg Ile Glu Leu
705                 710                 715                 720 aag ggc atc gac ttc aag gag gac ggc aac atc ctg ggg cac aag ctg       2208
Lys Gly Ile Asp Phe Lys Glu Asp Gly Asn Ile Leu Gly His Lys Leu
                725                 730                 735 gag tac aac tac aac agc cac aac gtc tat atc atg gcc gac aag cag       2256
Glu Tyr Asn Tyr Asn Ser His Asn Val Tyr Ile Met Ala Asp Lys Gln
                740                 745                 750 aag aac ggc atc aag gtg aac ttc aag atc cgc cac aac atc gag gac       2304
Lys Asn Gly Ile Lys Val Asn Phe Lys Ile Arg His Asn Ile Glu Asp
            755                 760                 765 ggc agc gtg cag ctc gcc gac cac tac cag cag aac acc ccc atc ggc       2352
Gly Ser Val Gln Leu Ala Asp His Tyr Gln Gln Asn Thr Pro Ile Gly
            770                 775                 780 gac ggc ccc gtg ctg ctg ccc gac aac cac tac ctg agc tac cag tcc       2400
Asp Gly Pro Val Leu Leu Pro Asp Asn His Tyr Leu Ser Tyr Gln Ser
785                 790                 795                 800 gcc ctg agc aaa gac ccc aac gag aag cgc gat cac atg gtc ctg ctg       2448
Ala Leu Ser Lys Asp Pro Asn Glu Lys Arg Asp His Met Val Leu Leu
                805                 810                 815 gag ttc gtg acc gcc gcc ggg atc act ctc ggc atg gac gag ctg tac       2496
Glu Phe Val Thr Ala Ala Gly Ile Thr Leu Gly Met Asp Glu Leu Tyr
                820                 825                 830
``` aag taa                                                                                 2502
Lys <210> SEQ ID NO 4
<211> LENGTH: 40
<212> TYPE: PRT
<213> ORGANISM: Artificial Sequence
<220> FEATURE:
<223> OTHER INFORMATION: Insertion peptide

<400> SEQUENCE: 4

Gly Ser Thr Glu Pro Gly Leu Glu Glu Val Gly Glu Ile Glu Gln Lys
1               5                   10                  15

Gln Leu Gln Lys Arg Phe Gly Gly Phe Thr Gly Ala Arg Lys Ser Ala
            20                  25                  30

Arg Lys Leu Ala Asn Gln Gly Ser
        35                  40

<210> SEQ ID NO 5
<211> LENGTH: 40
<212> TYPE: PRT
<213> ORGANISM: Artificial Sequence
<220> FEATURE:
<223> OTHER INFORMATION: Insertion peptide

<400> SEQUENCE: 5

Gly Ser Leu Val Gly Gln Leu Pro Gly Arg Leu Pro Gly Pro Gly Glu
1               5                   10                  15

Ala Pro Glu Pro Leu Leu Gln Leu Phe Leu Leu Asn Leu Pro His Leu
            20                  25                  30

Leu Gln Ala Gly Leu Cys Gly Ser
        35                  40

<210> SEQ ID NO 6
<211> LENGTH: 53
<212> TYPE: DNA
<213> ORGANISM: Artificial Sequence
<220> FEATURE:
<223> OTHER INFORMATION: primer 1

<400> SEQUENCE: 6
cacaagcttc cattgtgctg gatgaagata taattctgt ctgttatatt ggc          53

<210> SEQ ID NO 7
<211> LENGTH: 33
<212> TYPE: DNA
<213> ORGANISM: Artificial Sequence
<220> FEATURE:
<223> OTHER INFORMATION: primer 2

<400> SEQUENCE: 7
tgtggatcct tgacattcag gtggtacttc tag                               33

<210> SEQ ID NO 8
<211> LENGTH: 48
<212> TYPE: DNA
<213> ORGANISM: Artificial Sequence
<220> FEATURE:
<223> OTHER INFORMATION: primer 3

<400> SEQUENCE: 8
caagcttgcg gccgcaggat ccgtgagcaa gggcgaggag ctgttcac               48

<210> SEQ ID NO 9

-continued

```
<211> LENGTH: 38
<212> TYPE: DNA
<213> ORGANISM: Artificial Sequence
<220> FEATURE:
<223> OTHER INFORMATION: primer 4

<400> SEQUENCE: 9
taccattgtg ctggatggtg agcaagggcg aggagctg                          38

<210> SEQ ID NO 10
<211> LENGTH: 16
<212> TYPE: PRT
<213> ORGANISM: Artificial Sequence
<220> FEATURE:
<223> OTHER INFORMATION: partial mammalian sequence

<400> SEQUENCE: 10

Ser Glu Gln Lys Gln Leu Gln Lys Arg Phe Gly Gly Phe Thr Gly Gly
1               5                   10                  15
```